United States Patent
Tsuboyama et al.

(10) Patent No.: US 6,783,873 B2
(45) Date of Patent: Aug. 31, 2004

(54) METAL COORDINATION COMPOUND AND ORGANIC LUMINESCENCE DEVICE

(75) Inventors: Akira Tsuboyama, Sagamihara (JP); Hidemasa Mizutani, Sagamihara (JP); Shinjiro Okada, Isehara (JP); Takao Takiguchi, Tokyo (JP); Seishi Miura, Sagamihara (JP); Takashi Moriyama, Kawasaki (JP); Satoshi Igawa, Fujisawa (JP); Jun Kamatani, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 28 days.

(21) Appl. No.: 10/167,707

(22) Filed: Jun. 13, 2002

(65) Prior Publication Data

US 2003/0152802 A1 Aug. 14, 2003

(30) Foreign Application Priority Data

Jun. 19, 2001 (JP) .......................................... 2001/184631
May 23, 2002 (JP) .......................................... 2002/148698

(51) Int. Cl.$^7$ ........................... H05B 33/14; C09K 11/06
(52) U.S. Cl. ........................ 428/690; 428/917; 313/504; 252/301.16; 257/103; 544/225; 546/2; 546/4; 548/101; 548/108
(58) Field of Search .............................. 428/690, 917; 313/504, 506; 252/301.16; 257/102, 103; 544/225; 546/2, 4; 548/101, 108

(56) References Cited

U.S. PATENT DOCUMENTS

| | | | |
|---|---|---|---|
| 2001/0019782 A1 * | 9/2001 | Igarashi et al. | 428/690 |
| 2002/0063516 A1 | 5/2002 | Tsuboyama et al. | 313/504 |
| 2002/0064681 A1 | 5/2002 | Takiguchi et al. | 428/690 |
| 2002/0064683 A1 | 5/2002 | Okada et al. | 428/690 |
| 2002/0068190 A1 | 6/2002 | Tsuboyama et al. | 428/690 |
| 2002/0079830 A1 * | 6/2002 | Brunner et al. | 313/498 |

OTHER PUBLICATIONS

Iwao Omae, Organometallic Intramolecular–coordination Compounds (Journal of Organometallic Chemistry; 18), Elsevier Science Publishers B.V., 1986, p. 45, (no month).*

Benedikt Schlicke et al., "Photonic Wires of Nanometric Dimensions. Electronic Energy Transfer in Rigid Rodlike Ru(bpy) . . . ", J. Am. Chem. Soc., vol. 121, pp. 4207–4214 (published on Web Apr. 15, 1999).*

D.F. O'Brien et al., "Improved Energy Transfer in Electrophosphorescent Devices," 74(3) *Applied Phys. Lett.* 442–444 (Jan. 18, 1999).

M.A. Baldo et al. "Very High–Efficiency Green Organic Light–Emitting Devices Based on Electrophosphorescence," 75(1) *Applied Phys. Lett.* 4–6 (Jul. 5, 1999).

C.H. Chen et al., "Recent Developments in Molecular Organic Electroluminescent Materials," 125 *Macromol. Symp.* 1–48 (1997), no month.

* cited by examiner

Primary Examiner—Marie Yamnitzky
(74) Attorney, Agent, or Firm—Fitzpatrick, Cella, Harper & Scinto

(57) ABSTRACT

A metal coordination compound having a binuclear molecular structure represented by the following formula (1):

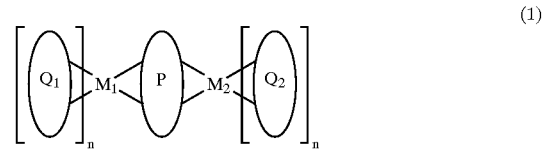

(1)

wherein M1 and M2 independently denotes a metal atom selected from the group consisting of Ir, Pt, Rh, Pd, Ru and Os; P is a quadridentate ligand connected to M1 and M1; Q1 is a bidentate ligand connected to M1; Q2 is a bidentate ligand connected to M2; and n is 1 or 2.

9 Claims, 3 Drawing Sheets

METAL COORDINATION COMPOUND AND ORGANIC LUMINESCENCE DEVICE

FIELD OF THE INVENTION AND RELATED ART

The present invention relates to a metal coordination compound having a binuclear molecular structure and an organic luminescence device using the metal coordination compound, more particularly to an organic luminescence device exhibiting a long life and a high luminescence efficiency by using the metal coordination compound as a luminescence material.

An extensive study on an organic electroluminescence (EL) device for device formation as a luminescence device of a high-speed responsiveness and a high efficiency, has been conducted.

As described in detail in, e.g., Macromol. Symp. 125, 1–48 (1997), an organic EL device generally has a structure comprising upper and lower two electrodes and a plurality of organic film layers between the electrodes formed on a transparent substrate. Basic structures thereof are shown in FIGS. 1A–1D.

As shown in these figures, an organic EL device generally has a structure comprising a transparent electrode 14, a metal electrode 11, and a plurality of organic film layers therebetween on a transparent substrate 15.

In the device of FIG. 1A, the organic layers comprise a luminescence layer 12 and a hole-transporting layer 13. For the transparent electrode 14, ITO, etc., having a large work function are used, for providing a good hole-injection characteristic from the transparent electrode 14 to the hole-transporting layer 13. For the metal electrode 11, a metal, such as aluminum, magnesium or an alloy of these, having a small work function is used for providing a good electron-injection characteristic to the organic film layers. These electrodes have a thickness of 50–200 nm.

For the luminescence layer 12, aluminum quinolynol complexes (a representative example thereof is Alq3 shown hereinafter), etc., having an electron-transporting characteristic and luminescence characteristic are used. For the hole-transporting layer 13, biphenyldiamine derivatives (a representative example thereof is α-NPD shown hereinafter), etc., having an electron-donative characteristic are used.

The above-structured device has a rectifying characteristic, and when an electric field is applied between the metal electrode 11 as a cathode and the transparent electrode 14 as an anode, electrons are injected from the metal electrode 11 into the luminescence layer 12 and holes are injected from the transparent electrode 15. The injected holes and electrons are recombined within the luminescence layer 12 to form excitons and cause luminescence. At this time, the hole-transporting layer 13 functions as an electron-blocking layer to increase the recombination efficiency at a boundary between the luminescence layer 12 and hole-transporting layer 13, thereby increasing the luminescence efficiency.

Further, in the structure of FIG. 1B, an electron-transporting layer 16 is disposed between the metal electrode 11 and the luminescence layer 12. By separating the luminescence and the electron and hole-transportation to provide a more effective carrier blocking structure, effective luminescence can be performed. For the electron-transporting layer 16, an electron-transporting material, such as an oxadiazole derivative, is used.

Further, in the structure of FIG. 1D, a luminescence layer 12 as a single organic layer is disposed between the metal electrode 12 and the transparent electrode 14. This structure is advantageous in view of productivity of the resultant device, and applicable to production processes using vapor deposition and wet coating. The luminescence layer 12 used in this structure is required to exhibit electron and hole transfer performances in addition to a luminescence performance.

Known luminescence processes used heretofore in organic EL devices include one utilizing an excited singlet state and one utilizing an excited triplet state, and the transition from the former state to the ground state is called "fluorescence" and the transition from the latter state to the ground state is called "phosphorescence". And the substances in these excited states are called a singlet exciton and a triplet exciton, respectively.

In most of the organic luminescence devices studied heretofore, fluorescence caused by the transition from the excited singlet state to the ground state, has been utilized. On the other hand, in recent years, devices utilizing phosphorescence via triplet excitons have been studied.

Representative published literature may include:

Article 1: Improved energy transfer in electrophosphorescent device (D. F. O'Brien, et al., Applied Physics Letters, Vol. 74, No. 3, p. 422-(1999)); and Article 2: Very high-efficiency green organic light-emitting devices based on electrophosphorescence (M. A. Baldo, et al., Applied Physics Letters, Vol. 75, No. 1, p. 4-(1999)).

In these articles, a structure including 4 organic layers devices as shown in FIG. 1C has been principally used, including, from the anode side, a hole-transporting layer 13, a luminescence layer 12, an exciton diffusion-prevention layer 17 and an electron-transporting layer 16. Materials used therein include carrier-transporting materials and phosphorescent materials, of which the names and structures are shown below together with their abbreviations.

Alq3: aluminum quinolinol complex

α-NPD: N4,N4'-di-naphthalene-1-yl-N4,N4'-diphenyl-biphenyl-4,4'-diamine

CBP: 4,4'-N,N'-dicarbazole-biphenyl

BCP: 2,9-dimethyl-4,7-diphenyl-1,10-phenanthroline

PtOEP: platinum-octaethylporphyrin complex

Ir(ppy)₃: iridium-phenylpyrimidine complex

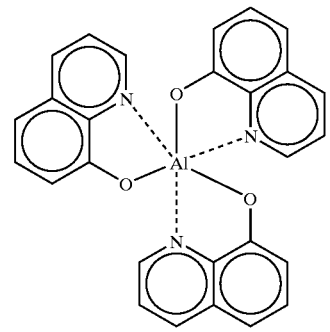

Alq3

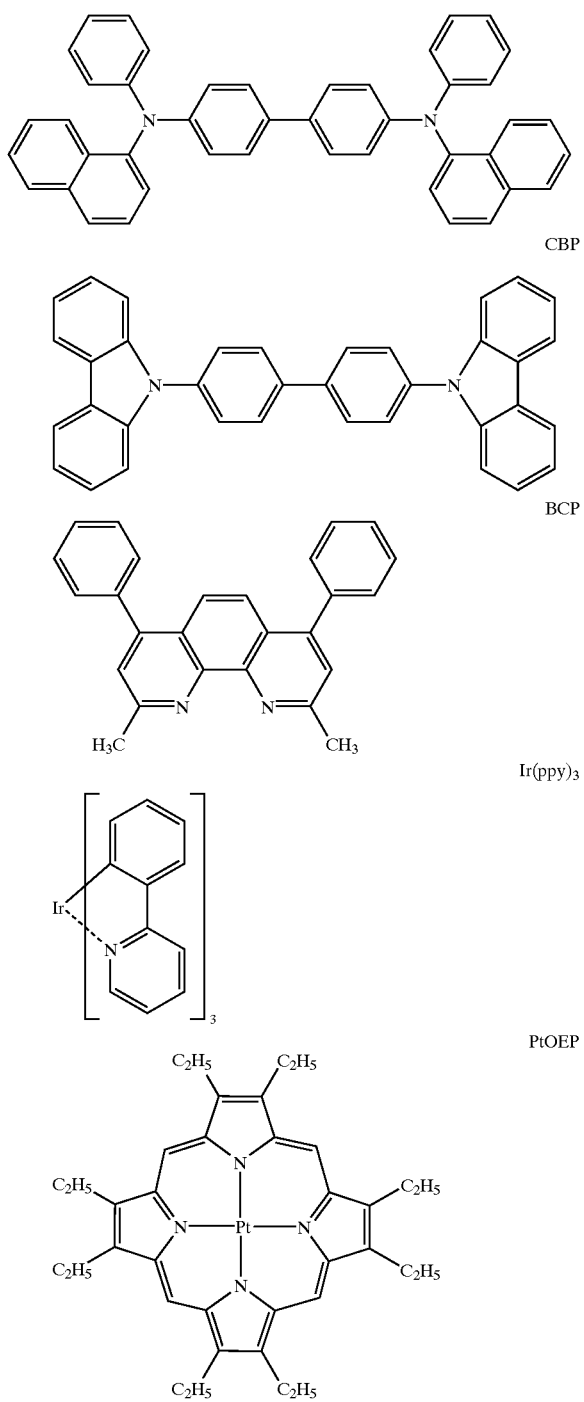

Such a phosphorescent material is particularly noted at present because it is expected to provide a luminescence efficiency of 100% in principle being four times that of a fluorescent material.

However, such an organic luminescence device utilizing phosphorescence is generally required to be further improved regarding the deterioration of luminescence efficiency and device stability.

The reason of the deterioration has not been fully clarified, but the present inventors consider as follows based on the mechanism of phosphorescence.

Generally, in a phosphorescent material, a life of the triplet excitons is longer by three or more digits than the life of a-singlet exciton. More specifically, molecules are held in a high-energy excited state for a longer period to cause reaction with surrounding materials, polymer formation among the excitons, a change in fine molecular structure, and a change in structure of the surrounding materials.

For this reason, a luminescence center material for use in the phosphorescent-type luminescence device is desired to exhibit a high-efficiency luminescence and a high stability. Further, a phosphorescent material providing a high phosphorescence yield and allowing control of emission wavelength has not been proposed heretofore. Accordingly, such a phosphorescent material is desired to be provided.

SUMMARY OF THE INVENTION

In view of the above-mentioned circumstances, an object of the present invention is to provide a phosphorescent material allowing a high phosphorescence yield and control of emission wavelength.

Another object of the present invention is to provide an organic luminescence device using the phosphorescent material capable of producing high-efficiency luminescence and holding a high luminescence for a long period.

According to the present invention, there is provided a metal coordination compound represented by the following formula (1):

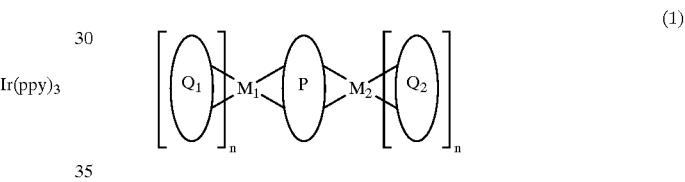

(1)

wherein M1 and M2 independently denotes a metal atom selected from the group consisting of Ir, Pt, Rh, Pd, Ru and Os; P is a quadridentate ligand connected to M1 and M1; Q1 is a bidentate ligand connected to M1; Q2 is a bidentate ligand connected to M2; and n is 1 or 2.

In a preferred embodiment, the bidentate ligand Q1 is represented by formula (2) shown below and the bidentate ligand Q2 is represented by formula (3) shown below:

(2)

(3)

wherein CyN1 and CyN2 are each cyclic group capable of having a substituent, including a nitrogen atom and bonded to the metal atom M1 or M2 via the nitrogen atom; CyC1 and CyC2 are each cyclic group capable of having a substituent, including a carbon atom and bonded to the metal atom M1 or M2 via the carbon atom with the proviso that the cyclic group CyN1 and the cyclic group CyC1 are bonded to each other via a covalent bond and the cyclic group CyN2 and the cyclic group CyC2 are bonded to each other via covalent bond;

the optional substituent of the cyclic groups is selected from a halogen atom; cyano group; a nitro group; a trialkylsilyl group of which the alkyl groups are independently a linear or branched alkyl group having 1 to 8 carbon atoms; a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom; and an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom).

In the above-mentioned formula (1), the quadridentate ligand P may preferably be connected to the metal atoms M1 and M2 each via a carbon atom, an oxygen atom or a nitrogen atom. The metal atom M1 is identical in species to the metal atom M2. The bidentate ligand Q1 may preferably be identical to the bidentate ligand Q2. The bidentate ligands Q1 and Q2 may preferably be respectively a carrier-transporting ligand or an energy-trapping ligand and the quadridentate ligand P may preferably be a luminescent ligand.

According to the present invention, there is also provided an organic luminescence device, comprising: a pair of electrodes disposed on a substrate, and a luminescence layer comprising at least one organic compound disposed between the electrodes, said organic compound comprising at least one species of a metal coordination compound of the formula (1) described above.

These and other objects, features and advantages of the present invention will become more apparent upon a consideration of the following description of the preferred embodiments of the present invention taken in conjunction with the accompanying drawings.

DETAILED DESCRIPTION OF THE PREFERRED EMBODIMENTS

Figure 1A:
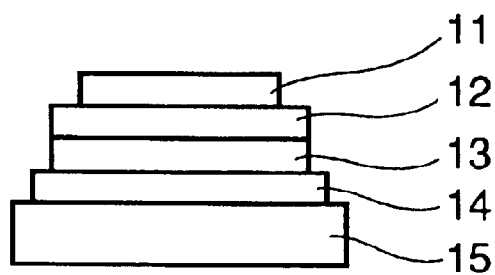
FIGS. 1A–1D respectively illustratively an embodiment of a film layer structure of the organic luminescence device according to the present invention.
Figure 1B:
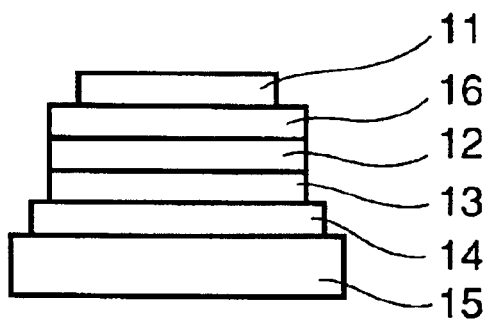

In order to improve a luminescence efficiency of the organic EL device (organic luminescence device), a luminescence center material per se is required to provide a higher yield of luminescence quantum. In addition thereto, when a luminescence layer is comprised of a luminescent material as a guest material and a base or matrix material as a host material, an efficient energy transfer between host material molecules and/or between host material molecule and guest material molecule is also an important factor.

Further, the above-described luminescent deterioration in energized state may presumably relate to the luminescent center material per se or an environmental change thereof by its surrounding molecules.

The metal coordination compound of the formula (1) used in the present invention produces phosphorescence, and its lowest excited state is believed to be an MLCT* (metal-to-ligand charge transfer) excited state or $\pi$–$\pi$* excited state in a triplet state, and phosphorescence is caused at the time of transition from such a state to the ground state.

The luminescence material of the present invention exhibited a high phosphorescence yield of at least 0.01 and a short phosphorescence life of 1–100 $\mu$sec.

The shorter phosphorescence life is necessary to provide a resultant EL device with a higher luminescence efficiency. This is because the longer phosphorescence life increases molecules placed in their excited triplet state which is a waiting state for phosphorescence, thus lowering the resultant luminescence efficiency particularly at a higher current density.

Accordingly, the metal coordination compound of formula (1) according to the present invention is a suitable luminescent material for an EL device with a higher phosphorescence yield and a shorter phosphorescence life.

Further, the shorter phosphorescence life leads to a shorter retention time of molecules in the excited triplet state, i.e., a high-energy state, thus expecting provision of less device deterioration and high durability to the resultant device.

The metal coordination compound of the formula (1) used as the luminescent material is binuclear metal coordination compound having two metal atoms in one molecule, thereby to exhibit a stable high-luminescent characteristic. As a result, the metal coordination compound effectively used in the luminescence layer of the organic EL device, particularly being suitable as a phosphorescent material for an organic luminescence device utilizing phosphorescence.

The specific reason thereof may be considered as follows.

(1) Phosphorescence is emission of light at the time of transition from the excited triplet state to the ground state. In a deactivation process by the phosphorescence, spin is forbidden according to quantum mechanical first-order approximation. However, a heavy atom is present within a molecule to enhance spin-orbit interaction, whereby the forbidden spin is allowed. The spin-orbit interaction becomes stronger as a heavier atom is used. The metal coordination compound used in the present invention has two metal atoms in one molecules, thus effectively encouraging the spin-orbit interaction to produce strong phosphorescence.

(2) In a molecular structure of the metal coordination compound of the present invention, the center quadridentate ligand P connecting two metal atoms is sterically surrounded by the two bidentate ligands Q1 and Q2, thus being separated from surrounding or ambient molecules. In the case where the center quadridentate ligand P relates to phosphorescence (luminescence), the quadridentate ligand P is guarded against the surrounding molecules. As a result, a probability of radiationless deactivation due to deactivation passage formed by the intermolecular interaction is considerably decreased thus allowing strong luminescence from the excited state of the metal coordination compound molecule having the center quadridentate ligand P.

(3) In the case of an organic EL device, it is important to effect smooth energy transfer from a host molecule to a luminescent guest molecule. In the metal coordination compound of the present invention, the surrounding ligands (the bidentate ligands) Q1 and Q2 function as an energy-trapping ligand liable to promote such energy transfer, and the center ligand (the quadridentate ligand) P functions as a luminescent ligand, thus allowing smooth energy transfer. Further, as described in (2), the center ligand P is guarded against other surrounding molecules, thus being less liable to cause radiationless deactivation to allow strong luminescence with a high luminescence efficiency.

Generally, even a compound producing strong luminescence in a dispersion state or a low-concentration solution is liable to cause concentration extinction in such a high-concentration state that molecules thereof are associated or concentrated, thus remarkably lowering a luminescence luminance. This is because energy transfer from an excited molecule to a surrounding molecule is caused to occur, thus being less liable to produce luminescence. In a conventional phosphorescence-type organic luminescence device, a luminescence layer is composed of a material comprising a mixture of a luminescent material and a carrier-transporting material. Accordingly, due to the above-mentioned concentration extinction, a weight proportion of the luminescent material has been restricted to at most 10%.

However, the luminescent material used in the present invention has a better concentration extinction-prevention performance, so that the luminescent material can be used in a dispersion state in a host material at a high concentration.

In the case where the metal coordination compound of the formula (1) is used as the luminescent material according to the present invention, the concentration extinction is effectively suppressed, thus resulting in a better luminescence efficiency even at a high concentration of the luminescence material. Accordingly, the dispersion concentration (weight proportion) of the luminescent material (the metal coordination compound of the formula (1)) can be increased up to above 10%. Further, it is possible to form a luminescence layer only of the metal coordination compound of the formula (1) (i.e., weight proportion =100%). Accordingly, by the use of the metal coordination compound of the formula (1) according to the present invention, a luminance of light emitted from a resultant organic luminescence device can be increased.

Energy levels of the above-mentioned respective ligands may be determined based on a combination of a ligand with a metal atom.

For example, in the case of a partial structure (Partial Chemical Structural Formula No. 20 shown hereinafter) having a phenyl-pyridine ligand and Ir as M, an energy level of the partial structure can be determined by measuring a triplet energy level of tri-phenylpyridine-iridium complex (Ir(ppy)$_3$ shown above). The triplet energy level at room temperature is ca. 2.4 eV. On the other hand, a partial structure having a phenylpyrimidine ligand (as in Partial Chemical Structural Formula No. 1) has a triplet energy level lower than 2.4 eV.

When a metal coordination compound of formula (1) (Example Compound No. 1 shown hereinafter) having a center quadridentate ligand P comprising the phenylpyrimidine ligand and surrounding bidentate ligands Q1 and Q2 each comprising the phenylpyridine ligand is used in an organic luminescence device (organic EL device), energy transfer from surrounding host molecules (other molecule) to the phenylpyridine ligands (Q1 and Q2) is first caused to occur to place the phenylpyridine ligands in an excited state. Thereafter, energy thereof is transferred within the metal coordination compound molecule to excite the center phenylpyrimidine ligand (P), thus producing luminescence.

Thus, in the case where the center ligand finally causes luminescence based on the above-mentioned energy transfer, it is important to appropriately select functional ligands as described above for preparing the metal coordination compound of the formula (1) according to the present invention.

(4) In the case of an organic EL device having a luminescence layer formed of a host material doped with a luminescent material, a resultant device characteristic is largely affected by a carrier-transporting performance of the luminescence material alone.

For example, ligands having partial structures (Partial Chemical Structural Formulas Nos. 20, 27, 28 and 34) exhibit a carrier-transporting performance, thus increasing a current value of the resultant device when compared with a device using the host material which is not doped with the luminescent material. This can be confirmed by evaluating current characteristics of organic EL devices using Ir complexes each having three identical charge-transporting ligands (e.g., having the particle structure of Particle Chemical Structural No. 20, 27, 28 or 34). The increase in current value described above is considered to be based on hopping transport of carrier between guest luminescent molecules. Accordingly, when a luminescence material is constituted by a combination of a carrier-transporting ligand for the surrounding bidentate ligands with a luminescent ligand for the center quadridentate ligand, a carrier transport is improved. In addition thereto, the center quadridentate ligand is sterically surrounded by the surrounding bidentate ligands as described above, thus reducing a deactivation probability based on intermolecular interaction to allow a high-efficient luminescence.

The organic luminescence device according to the present invention may preferably be an electric field emission device such that an organic compound layer comprising the metal coordination compound of the formula (1) is sandwiched between a pair of opposing electrodes as shown in FIGS. 1A–1D, and a voltage is applied between the electrodes to cause luminescence.

A high-efficiency luminescence device according to the present invention is applicable to a product requiring energy economization or a high luminance. More specifically, the luminescence device is applicable to a display apparatus, an illumination apparatus, a printer light source or a backlight for a liquid crystal display apparatus. As for a display apparatus, it allows a flat panel display which is light in weight and provides a highly recognizable display at a low energy consumption. The flat panel display may have a simple matrix structure having a plurality of pixels constituted by intersecting stripe electrode at right angles or an active matrix structure having a plurality of pixels each provided with, e.g., a thin film transistor (TFT) of amorphous silicon or polysilicon. As a printer light source, the luminescence device of the present invention can be used instead of a laser light source of a laser beam printer. Independently addressable devices are arranged in an array form to effect a desired exposure on a photosensitive drum thereby forming an image. The apparatus volume can be remarkably reduced by using the devices of the present invention. For the illumination apparatus or backlight, the energy economization effect according to the present invention can be expected.

Hereinbelow, some specific structural formulas (Example Compound Nos. 1–760) of metal coordination compounds represented by the formula (1) according to the present invention are shown in Tables 1–16 appearing hereinafter, which are however only representative examples and are not exhaustive. Partial Chemical Structural Formulas Nos. 1–16 for P and 20–34 for Q1 and Q2 used in the tables represent partial structures shown below, respectively. The following metal coordination compounds include positively charged compounds. Such positively charged compounds can be used as luminescence materials for the organic luminescence device of the present invention by neutralizing the compounds with counter anions, such as halogen ions, $PF_6^-$ and $ClO_4^-$.
1
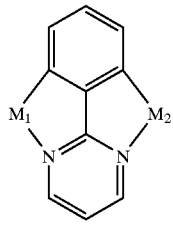
2
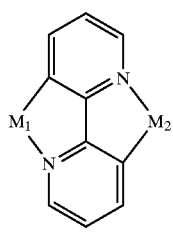
3
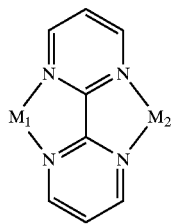
4
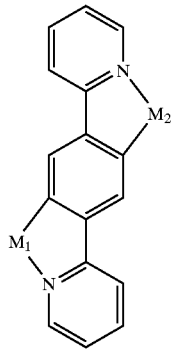
5
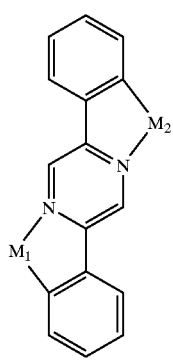
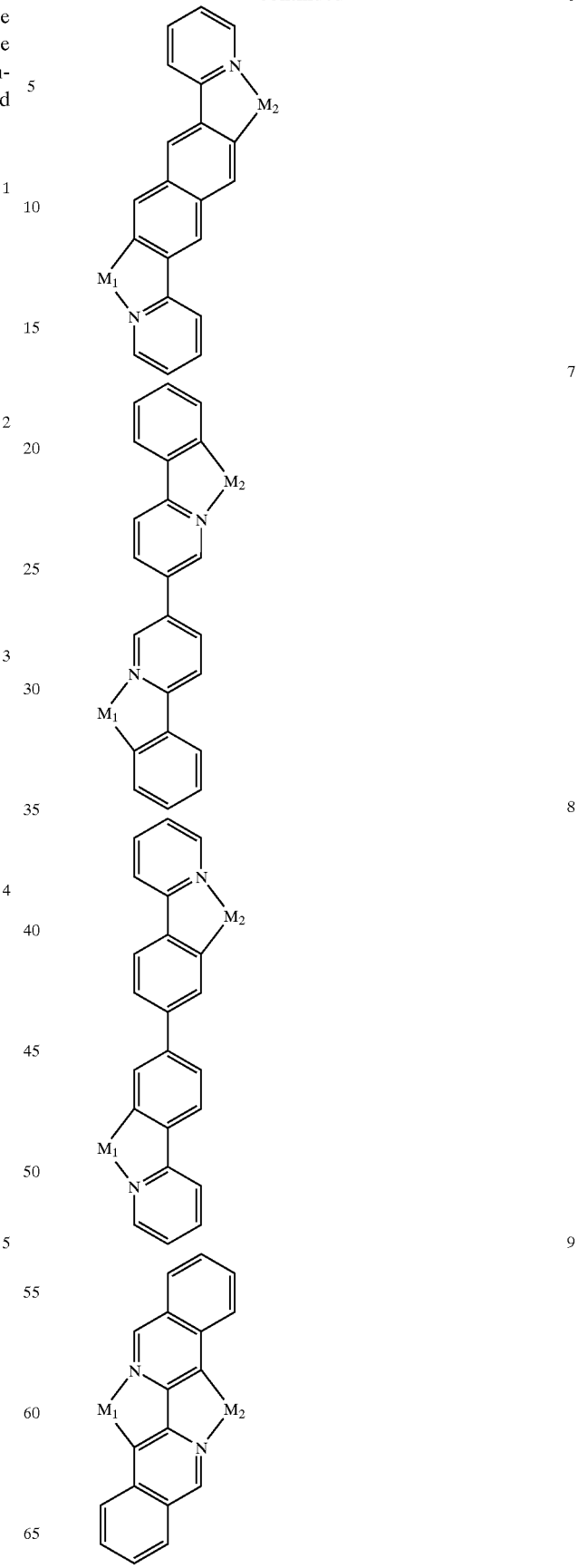

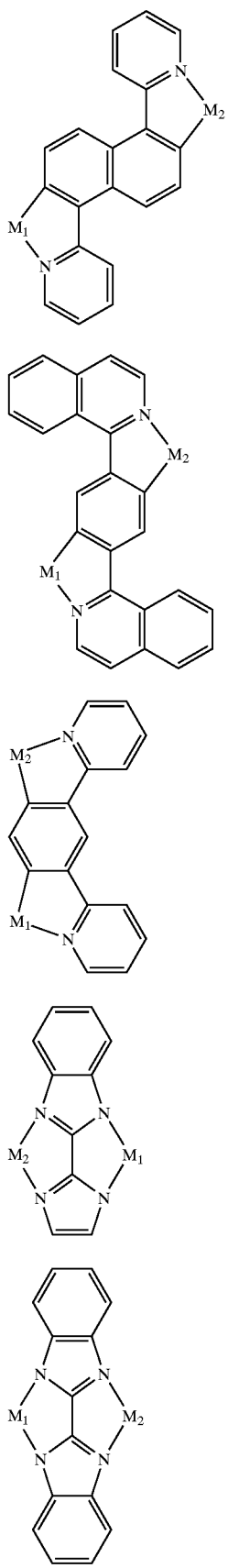
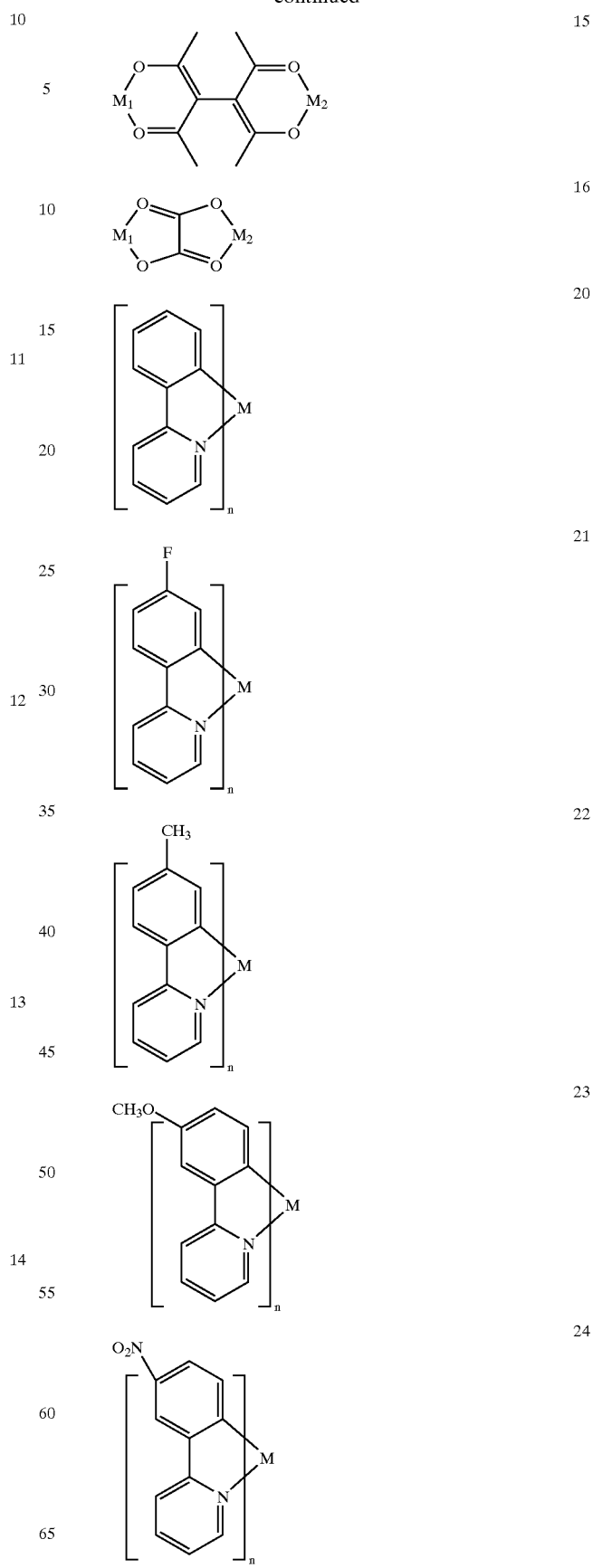

25
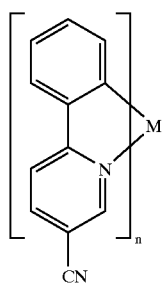
26
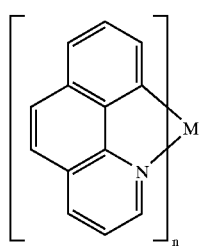
27
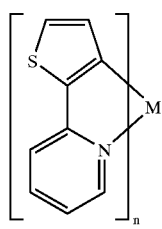
28
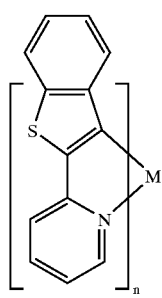
29
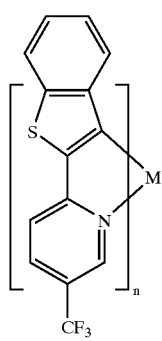
30
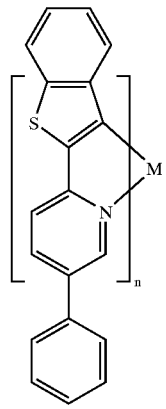
31
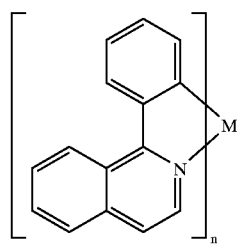
32
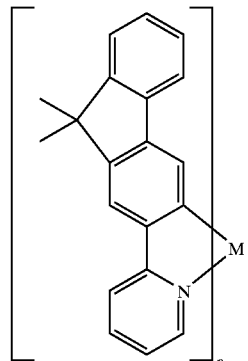
33
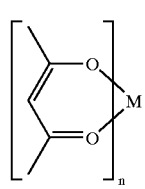
34
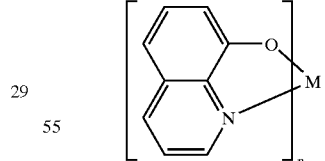
TABLE 1
| No | M1 | M2 | n | P | Q1 | Q2 |
|----|----|----|---|---|----|----|
| 1  | Ir | Ir | 2 | 1 | 20 | 20 |
| 2  | Ir | Ir | 2 | 1 | 21 | 21 |
| 3  | Ir | Ir | 2 | 1 | 22 | 22 |
| 4  | Ir | Ir | 2 | 1 | 23 | 23 |
| 5  | Ir | Ir | 2 | 1 | 24 | 24 |

TABLE 1-continued

| No | M1 | M2 | n | P | Q1 | Q2 |
|----|----|----|---|---|----|----|
| 6 | Ir | Ir | 2 | 1 | 25 | 25 |
| 7 | Ir | Ir | 2 | 1 | 26 | 26 |
| 8 | Ir | Ir | 2 | 1 | 27 | 27 |
| 9 | Ir | Ir | 2 | 1 | 28 | 28 |
| 10 | Ir | Ir | 2 | 1 | 29 | 29 |
| 11 | Ir | Ir | 2 | 1 | 30 | 30 |
| 12 | Ir | Ir | 2 | 1 | 31 | 31 |
| 13 | Ir | Ir | 2 | 1 | 32 | 32 |
| 14 | Ir | Ir | 2 | 1 | 33 | 33 |
| 15 | Ir | Ir | 2 | 1 | 34 | 34 |
| 16 | Ir | Ir | 2 | 2 | 20 | 20 |
| 17 | Ir | Ir | 2 | 2 | 21 | 21 |
| 18 | Ir | Ir | 2 | 2 | 22 | 22 |
| 19 | Ir | Ir | 2 | 2 | 23 | 23 |
| 20 | Ir | Ir | 2 | 2 | 24 | 24 |
| 21 | Ir | Ir | 2 | 2 | 25 | 25 |
| 22 | Ir | Ir | 2 | 2 | 26 | 26 |
| 23 | Ir | Ir | 2 | 2 | 27 | 27 |
| 24 | Ir | Ir | 2 | 2 | 28 | 28 |
| 25 | Ir | Ir | 2 | 2 | 29 | 29 |
| 26 | Ir | Ir | 2 | 2 | 30 | 30 |
| 27 | Ir | Ir | 2 | 2 | 31 | 31 |
| 28 | Ir | Ir | 2 | 2 | 32 | 32 |
| 29 | Ir | Ir | 2 | 2 | 33 | 33 |
| 30 | Ir | Ir | 2 | 2 | 34 | 34 |
| 31 | Ir | Ir | 2 | 3 | 20 | 20 |
| 32 | Ir | Ir | 2 | 3 | 21 | 21 |
| 33 | Ir | Ir | 2 | 3 | 22 | 22 |
| 34 | Ir | Ir | 2 | 3 | 23 | 23 |
| 35 | Ir | Ir | 2 | 3 | 24 | 24 |
| 36 | Ir | Ir | 2 | 3 | 25 | 25 |
| 37 | Ir | Ir | 2 | 3 | 26 | 26 |
| 38 | Ir | Ir | 2 | 3 | 27 | 27 |
| 39 | Ir | Ir | 2 | 3 | 28 | 28 |
| 40 | Ir | Ir | 2 | 3 | 29 | 29 |
| 41 | Ir | Ir | 2 | 3 | 30 | 30 |
| 42 | Ir | Ir | 2 | 3 | 31 | 31 |
| 43 | Ir | Ir | 2 | 3 | 32 | 32 |
| 44 | Ir | Ir | 2 | 3 | 33 | 33 |
| 45 | Ir | Ir | 2 | 3 | 34 | 34 |
| 46 | Ir | Ir | 2 | 4 | 20 | 20 |
| 47 | Ir | Ir | 2 | 4 | 21 | 21 |
| 48 | Ir | Ir | 2 | 4 | 22 | 22 |
| 49 | Ir | Ir | 2 | 4 | 23 | 23 |
| 50 | Ir | Ir | 2 | 4 | 24 | 24 |

TABLE 2

| No | M1 | M2 | n | P | Q1 | Q2 |
|----|----|----|---|---|----|----|
| 51 | Ir | Ir | 2 | 4 | 25 | 25 |
| 52 | Ir | Ir | 2 | 4 | 26 | 26 |
| 53 | Ir | Ir | 2 | 4 | 27 | 27 |
| 54 | Ir | Ir | 2 | 4 | 28 | 28 |
| 55 | Ir | Ir | 2 | 4 | 29 | 29 |
| 56 | Ir | Ir | 2 | 4 | 30 | 30 |
| 57 | Ir | Ir | 2 | 4 | 31 | 31 |
| 58 | Ir | Ir | 2 | 4 | 32 | 32 |
| 59 | Ir | Ir | 2 | 4 | 33 | 33 |
| 60 | Ir | Ir | 2 | 4 | 34 | 34 |
| 61 | Ir | Ir | 2 | 5 | 20 | 20 |
| 62 | Ir | Ir | 2 | 5 | 21 | 21 |
| 63 | Ir | Ir | 2 | 5 | 22 | 22 |
| 64 | Ir | Ir | 2 | 5 | 23 | 23 |
| 65 | Ir | Ir | 2 | 5 | 24 | 24 |
| 66 | Ir | Ir | 2 | 5 | 25 | 25 |
| 67 | Ir | Ir | 2 | 5 | 26 | 26 |
| 68 | Ir | Ir | 2 | 5 | 27 | 27 |
| 69 | Ir | Ir | 2 | 5 | 28 | 28 |
| 70 | Ir | Ir | 2 | 5 | 29 | 29 |
| 71 | Ir | Ir | 2 | 5 | 30 | 30 |
| 72 | Ir | Ir | 2 | 5 | 31 | 31 |
| 73 | Ir | Ir | 2 | 5 | 32 | 32 |
| 74 | Ir | Ir | 2 | 5 | 33 | 33 |

TABLE 2-continued

| No | M1 | M2 | n | P | Q1 | Q2 |
|----|----|----|---|---|----|----|
| 75 | Ir | Ir | 2 | 5 | 34 | 34 |
| 76 | Ir | Ir | 2 | 6 | 20 | 20 |
| 77 | Ir | Ir | 2 | 6 | 21 | 21 |
| 78 | Ir | Ir | 2 | 6 | 22 | 22 |
| 79 | Ir | Ir | 2 | 6 | 23 | 23 |
| 80 | Ir | Ir | 2 | 6 | 24 | 24 |
| 81 | Ir | Ir | 2 | 6 | 25 | 25 |
| 82 | Ir | Ir | 2 | 6 | 26 | 26 |
| 83 | Ir | Ir | 2 | 6 | 27 | 27 |
| 84 | Ir | Ir | 2 | 6 | 28 | 28 |
| 85 | Ir | Ir | 2 | 6 | 29 | 29 |
| 86 | Ir | Ir | 2 | 6 | 30 | 30 |
| 87 | Ir | Ir | 2 | 6 | 31 | 31 |
| 88 | Ir | Ir | 2 | 6 | 32 | 32 |
| 89 | Ir | Ir | 2 | 6 | 33 | 33 |
| 90 | Ir | Ir | 2 | 6 | 34 | 34 |
| 91 | Ir | Ir | 2 | 7 | 20 | 20 |
| 92 | Ir | Ir | 2 | 7 | 21 | 21 |
| 93 | Ir | Ir | 2 | 7 | 22 | 22 |
| 94 | Ir | Ir | 2 | 7 | 23 | 23 |
| 95 | Ir | Ir | 2 | 7 | 24 | 24 |
| 96 | Ir | Ir | 2 | 7 | 25 | 25 |
| 97 | Ir | Ir | 2 | 7 | 26 | 26 |
| 98 | Ir | Ir | 2 | 7 | 27 | 27 |
| 99 | Ir | Ir | 2 | 7 | 28 | 28 |
| 100 | Ir | Ir | 2 | 7 | 29 | 29 |

TABLE 3

| No | M1 | M2 | n | P | Q1 | Q2 |
|----|----|----|---|---|----|----|
| 101 | Ir | Ir | 2 | 7 | 30 | 30 |
| 102 | Ir | Ir | 2 | 7 | 31 | 31 |
| 103 | Ir | Ir | 2 | 7 | 32 | 32 |
| 104 | Ir | Ir | 2 | 7 | 33 | 33 |
| 105 | Ir | Ir | 2 | 7 | 34 | 34 |
| 106 | Ir | Ir | 2 | 8 | 20 | 20 |
| 107 | Ir | Ir | 2 | 8 | 21 | 21 |
| 108 | Ir | Ir | 2 | 8 | 22 | 22 |
| 109 | Ir | Ir | 2 | 8 | 23 | 23 |
| 110 | Ir | Ir | 2 | 8 | 24 | 24 |
| 111 | Ir | Ir | 2 | 8 | 25 | 25 |
| 112 | Ir | Ir | 2 | 8 | 26 | 26 |
| 113 | Ir | Ir | 2 | 8 | 27 | 27 |
| 114 | Ir | Ir | 2 | 8 | 28 | 28 |
| 115 | Ir | Ir | 2 | 8 | 29 | 29 |
| 116 | Ir | Ir | 2 | 8 | 30 | 30 |
| 117 | Ir | Ir | 2 | 8 | 31 | 31 |
| 118 | Ir | Ir | 2 | 8 | 32 | 32 |
| 119 | Ir | Ir | 2 | 8 | 33 | 33 |
| 120 | Ir | Ir | 2 | 8 | 34 | 34 |
| 121 | Ir | Ir | 2 | 9 | 20 | 20 |
| 122 | Ir | Ir | 2 | 9 | 21 | 21 |
| 123 | Ir | Ir | 2 | 9 | 22 | 22 |
| 124 | Ir | Ir | 2 | 9 | 23 | 23 |
| 125 | Ir | Ir | 2 | 9 | 24 | 24 |
| 126 | Ir | Ir | 2 | 9 | 25 | 25 |
| 127 | Ir | Ir | 2 | 9 | 26 | 26 |
| 128 | Ir | Ir | 2 | 9 | 27 | 27 |
| 129 | Ir | Ir | 2 | 9 | 28 | 28 |
| 130 | Ir | Ir | 2 | 9 | 29 | 29 |
| 131 | Ir | Ir | 2 | 9 | 30 | 30 |
| 132 | Ir | Ir | 2 | 9 | 31 | 31 |
| 133 | Ir | Ir | 2 | 9 | 32 | 32 |
| 134 | Ir | Ir | 2 | 9 | 33 | 33 |
| 135 | Ir | Ir | 2 | 9 | 34 | 34 |
| 136 | Ir | Ir | 2 | 10 | 20 | 20 |
| 137 | Ir | Ir | 2 | 10 | 21 | 21 |
| 138 | Ir | Ir | 2 | 10 | 22 | 22 |
| 139 | Ir | Ir | 2 | 10 | 23 | 23 |
| 140 | Ir | Ir | 2 | 10 | 24 | 24 |
| 141 | Ir | Ir | 2 | 10 | 25 | 25 |
| 142 | Ir | Ir | 2 | 10 | 26 | 26 |
| 143 | Ir | Ir | 2 | 10 | 27 | 27 |

TABLE 3-continued

| No | M1 | M2 | n | P | Q1 | Q2 |
|---|---|---|---|---|---|---|
| 144 | Ir | Ir | 2 | 10 | 28 | 28 |
| 145 | Ir | Ir | 2 | 10 | 29 | 29 |
| 146 | Ir | Ir | 2 | 10 | 30 | 30 |
| 147 | Ir | Ir | 2 | 10 | 31 | 31 |
| 148 | Ir | Ir | 2 | 10 | 32 | 32 |
| 149 | Ir | Ir | 2 | 10 | 33 | 33 |
| 150 | Ir | Ir | 2 | 10 | 34 | 34 |

TABLE 4

| No | M1 | M2 | n | P | Q1 | Q2 |
|---|---|---|---|---|---|---|
| 151 | Ir | Ir | 2 | 11 | 20 | 20 |
| 152 | Ir | Ir | 2 | 11 | 21 | 21 |
| 153 | Ir | Ir | 2 | 11 | 22 | 22 |
| 154 | Ir | Ir | 2 | 11 | 23 | 23 |
| 155 | Ir | Ir | 2 | 11 | 24 | 24 |
| 156 | Ir | Ir | 2 | 11 | 25 | 25 |
| 157 | Ir | Ir | 2 | 11 | 26 | 26 |
| 158 | Ir | Ir | 2 | 11 | 27 | 27 |
| 159 | Ir | Ir | 2 | 11 | 28 | 28 |
| 160 | Ir | Ir | 2 | 11 | 29 | 29 |
| 161 | Ir | Ir | 2 | 11 | 30 | 30 |
| 162 | Ir | Ir | 2 | 11 | 31 | 31 |
| 163 | Ir | Ir | 2 | 11 | 32 | 32 |
| 164 | Ir | Ir | 2 | 11 | 33 | 33 |
| 165 | Ir | Ir | 2 | 11 | 34 | 34 |
| 166 | Ir | Ir | 2 | 12 | 20 | 20 |
| 167 | Ir | Ir | 2 | 12 | 21 | 21 |
| 168 | Ir | Ir | 2 | 12 | 22 | 22 |
| 169 | Ir | Ir | 2 | 12 | 23 | 23 |
| 170 | Ir | Ir | 2 | 12 | 24 | 24 |
| 171 | Ir | Ir | 2 | 12 | 25 | 25 |
| 172 | Ir | Ir | 2 | 12 | 26 | 26 |
| 173 | Ir | Ir | 2 | 12 | 27 | 27 |
| 174 | Ir | Ir | 2 | 12 | 28 | 28 |
| 175 | Ir | Ir | 2 | 12 | 29 | 29 |
| 176 | Ir | Ir | 2 | 12 | 30 | 30 |
| 177 | Ir | Ir | 2 | 12 | 31 | 31 |
| 178 | Ir | Ir | 2 | 12 | 32 | 32 |
| 179 | Ir | Ir | 2 | 12 | 33 | 33 |
| 180 | Ir | Ir | 2 | 12 | 34 | 34 |
| 181 | Ir | Ir | 2 | 13 | 20 | 20 |
| 182 | Ir | Ir | 2 | 13 | 21 | 21 |
| 183 | Ir | Ir | 2 | 13 | 22 | 22 |
| 184 | Ir | Ir | 2 | 13 | 23 | 23 |
| 185 | Ir | Ir | 2 | 13 | 24 | 24 |
| 186 | Ir | Ir | 2 | 13 | 25 | 25 |
| 187 | Ir | Ir | 2 | 13 | 26 | 26 |
| 188 | Ir | Ir | 2 | 13 | 27 | 27 |
| 189 | Ir | Ir | 2 | 13 | 28 | 28 |
| 190 | Ir | Ir | 2 | 13 | 29 | 29 |
| 191 | Ir | Ir | 2 | 13 | 30 | 30 |
| 192 | Ir | Ir | 2 | 13 | 31 | 31 |
| 193 | Ir | Ir | 2 | 13 | 32 | 32 |
| 194 | Ir | Ir | 2 | 13 | 33 | 33 |
| 195 | Ir | Ir | 2 | 13 | 34 | 34 |
| 196 | Ir | Ir | 2 | 14 | 20 | 20 |
| 197 | Ir | Ir | 2 | 14 | 21 | 21 |
| 198 | Ir | Ir | 2 | 14 | 22 | 22 |
| 199 | Ir | Ir | 2 | 14 | 23 | 23 |
| 200 | Ir | Ir | 2 | 14 | 24 | 24 |

TABLE 5

| No | M1 | M2 | n | P | Q1 | Q2 |
|---|---|---|---|---|---|---|
| 201 | Ir | Ir | 2 | 14 | 25 | 25 |
| 202 | Ir | Ir | 2 | 14 | 26 | 26 |
| 203 | Ir | Ir | 2 | 14 | 27 | 27 |
| 204 | Ir | Ir | 2 | 14 | 28 | 28 |
| 205 | Ir | Ir | 2 | 14 | 29 | 29 |

TABLE 5-continued

| No | M1 | M2 | n | P | Q1 | Q2 |
|---|---|---|---|---|---|---|
| 206 | Ir | Ir | 2 | 14 | 30 | 30 |
| 207 | Ir | Ir | 2 | 14 | 31 | 31 |
| 208 | Ir | Ir | 2 | 14 | 32 | 32 |
| 209 | Ir | Ir | 2 | 14 | 33 | 33 |
| 210 | Ir | Ir | 2 | 14 | 34 | 34 |
| 211 | Ir | Ir | 2 | 15 | 20 | 20 |
| 212 | Ir | Ir | 2 | 15 | 21 | 21 |
| 213 | Ir | Ir | 2 | 15 | 22 | 22 |
| 214 | Ir | Ir | 2 | 15 | 23 | 23 |
| 215 | Ir | Ir | 2 | 15 | 24 | 24 |
| 216 | Ir | Ir | 2 | 15 | 25 | 25 |
| 217 | Ir | Ir | 2 | 15 | 26 | 26 |
| 218 | Ir | Ir | 2 | 15 | 27 | 27 |
| 219 | Ir | Ir | 2 | 15 | 28 | 28 |
| 220 | Ir | Ir | 2 | 15 | 29 | 29 |
| 221 | Ir | Ir | 2 | 15 | 30 | 30 |
| 222 | Ir | Ir | 2 | 15 | 31 | 31 |
| 223 | Ir | Ir | 2 | 15 | 32 | 32 |
| 224 | Ir | Ir | 2 | 15 | 33 | 33 |
| 225 | Ir | Ir | 2 | 15 | 34 | 34 |
| 226 | Ir | Ir | 2 | 16 | 20 | 20 |
| 227 | Ir | Ir | 2 | 16 | 21 | 21 |
| 228 | Ir | Ir | 2 | 16 | 22 | 22 |
| 229 | Ir | Ir | 2 | 16 | 23 | 23 |
| 230 | Ir | Ir | 2 | 16 | 24 | 24 |
| 231 | Ir | Ir | 2 | 16 | 25 | 25 |
| 232 | Ir | Ir | 2 | 16 | 26 | 26 |
| 233 | Ir | Ir | 2 | 16 | 27 | 27 |
| 234 | Ir | Ir | 2 | 16 | 28 | 28 |
| 235 | Ir | Ir | 2 | 16 | 29 | 29 |
| 236 | Ir | Ir | 2 | 16 | 30 | 30 |
| 237 | Ir | Ir | 2 | 16 | 31 | 31 |
| 238 | Ir | Ir | 2 | 16 | 32 | 32 |
| 239 | Ir | Ir | 2 | 16 | 33 | 33 |
| 240 | Ir | Ir | 2 | 16 | 34 | 34 |
| 241 | Ir | Ir | 2 | 1 | 20 | 23 |
| 242 | Ir | Ir | 2 | 1 | 20 | 27 |
| 243 | Ir | Ir | 2 | 1 | 20 | 28 |
| 244 | Ir | Ir | 2 | 1 | 20 | 33 |
| 245 | Ir | Ir | 2 | 1 | 20 | 34 |
| 246 | Ir | Ir | 2 | 1 | 27 | 33 |
| 247 | Ir | Ir | 2 | 1 | 27 | 34 |
| 248 | Ir | Ir | 2 | 2 | 20 | 23 |
| 249 | Ir | Ir | 2 | 2 | 20 | 27 |
| 250 | Ir | Ir | 2 | 2 | 20 | 28 |

TABLE 6

| No | M1 | M2 | n | P | Q1 | Q2 |
|---|---|---|---|---|---|---|
| 251 | Ir | Ir | 2 | 2 | 20 | 33 |
| 252 | Ir | Ir | 2 | 2 | 20 | 34 |
| 253 | Ir | Ir | 2 | 2 | 27 | 33 |
| 254 | Ir | Ir | 2 | 2 | 27 | 34 |
| 255 | Ir | Ir | 2 | 4 | 20 | 23 |
| 256 | Ir | Ir | 2 | 4 | 20 | 27 |
| 257 | Ir | Ir | 2 | 4 | 20 | 28 |
| 258 | Ir | Ir | 2 | 4 | 20 | 33 |
| 259 | Ir | Ir | 2 | 4 | 20 | 34 |
| 260 | Ir | Ir | 2 | 4 | 27 | 33 |
| 261 | Ir | Ir | 2 | 4 | 27 | 34 |
| 262 | Ir | Ir | 2 | 10 | 20 | 23 |
| 263 | Ir | Ir | 2 | 10 | 20 | 27 |
| 264 | Ir | Ir | 2 | 10 | 20 | 28 |
| 265 | Ir | Ir | 2 | 10 | 20 | 33 |
| 266 | Ir | Ir | 2 | 10 | 20 | 34 |
| 267 | Ir | Ir | 2 | 10 | 27 | 33 |
| 268 | Ir | Ir | 2 | 10 | 27 | 34 |
| 269 | Ir | Ir | 2 | 15 | 20 | 23 |
| 270 | Ir | Ir | 2 | 15 | 20 | 27 |
| 271 | Ir | Ir | 2 | 15 | 20 | 28 |
| 272 | Ir | Ir | 2 | 15 | 20 | 33 |
| 273 | Ir | Ir | 2 | 15 | 20 | 34 |
| 274 | Ir | Ir | 2 | 15 | 27 | 33 |

TABLE 6-continued

| No  | M1 | M2 | n | P  | Q1 | Q2 |
|-----|----|----|---|----|----|----|
| 275 | Ir | Ir | 2 | 15 | 27 | 34 |
| 276 | Rh | Rh | 2 | 1  | 20 | 20 |
| 277 | Rh | Rh | 2 | 1  | 21 | 21 |
| 278 | Rh | Rh | 2 | 1  | 22 | 22 |
| 279 | Rh | Rh | 2 | 1  | 23 | 23 |
| 280 | Rh | Rh | 2 | 1  | 24 | 24 |
| 281 | Rh | Rh | 2 | 1  | 25 | 25 |
| 282 | Rh | Rh | 2 | 1  | 26 | 26 |
| 283 | Rh | Rh | 2 | 1  | 27 | 27 |
| 284 | Rh | Rh | 2 | 1  | 28 | 28 |
| 285 | Rh | Rh | 2 | 1  | 29 | 29 |
| 286 | Rh | Rh | 2 | 1  | 30 | 30 |
| 287 | Rh | Rh | 2 | 1  | 31 | 31 |
| 288 | Rh | Rh | 2 | 1  | 32 | 32 |
| 289 | Rh | Rh | 2 | 1  | 33 | 33 |
| 290 | Rh | Rh | 2 | 1  | 34 | 34 |
| 291 | Rh | Rh | 2 | 2  | 20 | 20 |
| 292 | Rh | Rh | 2 | 2  | 21 | 21 |
| 293 | Rh | Rh | 2 | 2  | 22 | 22 |
| 294 | Rh | Rh | 2 | 2  | 23 | 23 |
| 295 | Rh | Rh | 2 | 2  | 24 | 24 |
| 296 | Rh | Rh | 2 | 2  | 25 | 25 |
| 297 | Rh | Rh | 2 | 2  | 26 | 26 |
| 298 | Rh | Rh | 2 | 2  | 27 | 27 |
| 299 | Rh | Rh | 2 | 2  | 28 | 28 |
| 300 | Rh | Rh | 2 | 2  | 29 | 29 |

TABLE 7

| No  | M1 | M2 | n | P | Q1 | Q2 |
|-----|----|----|---|---|----|----|
| 301 | Rh | Rh | 2 | 2 | 30 | 30 |
| 302 | Rh | Rh | 2 | 2 | 31 | 31 |
| 303 | Rh | Rh | 2 | 2 | 32 | 32 |
| 304 | Rh | Rh | 2 | 2 | 33 | 33 |
| 305 | Rh | Rh | 2 | 2 | 34 | 34 |
| 306 | Rh | Rh | 2 | 3 | 20 | 20 |
| 307 | Rh | Rh | 2 | 3 | 21 | 21 |
| 308 | Rh | Rh | 2 | 3 | 22 | 22 |
| 309 | Rh | Rh | 2 | 3 | 23 | 23 |
| 310 | Rh | Rh | 2 | 3 | 24 | 24 |
| 311 | Rh | Rh | 2 | 3 | 25 | 25 |
| 312 | Rh | Rh | 2 | 3 | 26 | 26 |
| 313 | Rh | Rh | 2 | 3 | 27 | 27 |
| 314 | Rh | Rh | 2 | 3 | 28 | 28 |
| 315 | Rh | Rh | 2 | 3 | 29 | 29 |
| 316 | Rh | Rh | 2 | 3 | 30 | 30 |
| 317 | Rh | Rh | 2 | 3 | 31 | 31 |
| 318 | Rh | Rh | 2 | 3 | 32 | 32 |
| 319 | Rh | Rh | 2 | 3 | 33 | 33 |
| 320 | Rh | Rh | 2 | 3 | 34 | 34 |
| 321 | Rh | Rh | 2 | 4 | 20 | 20 |
| 322 | Rh | Rh | 2 | 4 | 21 | 21 |
| 323 | Rh | Rh | 2 | 4 | 22 | 22 |
| 324 | Rh | Rh | 2 | 4 | 23 | 23 |
| 325 | Rh | Rh | 2 | 4 | 24 | 24 |
| 326 | Rh | Rh | 2 | 4 | 25 | 25 |
| 327 | Rh | Rh | 2 | 4 | 26 | 26 |
| 328 | Rh | Rh | 2 | 4 | 27 | 27 |
| 329 | Rh | Rh | 2 | 4 | 28 | 28 |
| 330 | Rh | Rh | 2 | 4 | 29 | 29 |
| 331 | Rh | Rh | 2 | 4 | 30 | 30 |
| 332 | Rh | Rh | 2 | 4 | 31 | 31 |
| 333 | Rh | Rh | 2 | 4 | 32 | 32 |
| 334 | Rh | Rh | 2 | 4 | 33 | 33 |
| 335 | Rh | Rh | 2 | 4 | 34 | 34 |
| 336 | Rh | Rh | 2 | 5 | 20 | 20 |
| 337 | Rh | Rh | 2 | 5 | 21 | 21 |
| 338 | Rh | Rh | 2 | 5 | 22 | 22 |
| 339 | Rh | Rh | 2 | 5 | 23 | 23 |
| 340 | Rh | Rh | 2 | 5 | 24 | 24 |
| 341 | Rh | Rh | 2 | 5 | 25 | 25 |
| 342 | Rh | Rh | 2 | 5 | 26 | 26 |
| 343 | Rh | Rh | 2 | 5 | 27 | 27 |

TABLE 7-continued

| No  | M1 | M2 | n | P | Q1 | Q2 |
|-----|----|----|---|---|----|----|
| 344 | Rh | Rh | 2 | 5 | 28 | 28 |
| 345 | Rh | Rh | 2 | 5 | 29 | 29 |
| 346 | Rh | Rh | 2 | 5 | 30 | 30 |
| 347 | Rh | Rh | 2 | 5 | 31 | 31 |
| 348 | Rh | Rh | 2 | 5 | 32 | 32 |
| 349 | Rh | Rh | 2 | 5 | 33 | 33 |
| 350 | Rh | Rh | 2 | 5 | 34 | 34 |

TABLE 8

| No  | M1 | M2 | n | P  | Q1 | Q2 |
|-----|----|----|---|----|----|----|
| 351 | Rh | Rh | 2 | 6  | 20 | 20 |
| 352 | Rh | Rh | 2 | 6  | 21 | 21 |
| 353 | Rh | Rh | 2 | 6  | 22 | 22 |
| 354 | Rh | Rh | 2 | 6  | 23 | 23 |
| 355 | Rh | Rh | 2 | 6  | 24 | 24 |
| 356 | Rh | Rh | 2 | 6  | 25 | 25 |
| 357 | Rh | Rh | 2 | 6  | 26 | 26 |
| 358 | Rh | Rh | 2 | 6  | 27 | 27 |
| 359 | Rh | Rh | 2 | 6  | 28 | 28 |
| 360 | Rh | Rh | 2 | 6  | 29 | 29 |
| 361 | Rh | Rh | 2 | 6  | 30 | 30 |
| 362 | Rh | Rh | 2 | 6  | 31 | 31 |
| 363 | Rh | Rh | 2 | 6  | 32 | 32 |
| 364 | Rh | Rh | 2 | 6  | 33 | 33 |
| 365 | Rh | Rh | 2 | 6  | 34 | 34 |
| 366 | Rh | Rh | 2 | 9  | 20 | 20 |
| 367 | Rh | Rh | 2 | 9  | 21 | 21 |
| 368 | Rh | Rh | 2 | 9  | 22 | 22 |
| 369 | Rh | Rh | 2 | 9  | 23 | 23 |
| 370 | Rh | Rh | 2 | 9  | 24 | 24 |
| 371 | Rh | Rh | 2 | 9  | 25 | 25 |
| 372 | Rh | Rh | 2 | 9  | 26 | 26 |
| 373 | Rh | Rh | 2 | 9  | 27 | 27 |
| 374 | Rh | Rh | 2 | 9  | 28 | 28 |
| 375 | Rh | Rh | 2 | 9  | 29 | 29 |
| 376 | Rh | Rh | 2 | 9  | 30 | 30 |
| 377 | Rh | Rh | 2 | 9  | 31 | 31 |
| 378 | Rh | Rh | 2 | 9  | 32 | 32 |
| 379 | Rh | Rh | 2 | 9  | 33 | 33 |
| 380 | Rh | Rh | 2 | 9  | 34 | 34 |
| 381 | Rh | Rh | 2 | 10 | 20 | 20 |
| 382 | Rh | Rh | 2 | 10 | 21 | 21 |
| 383 | Rh | Rh | 2 | 10 | 22 | 22 |
| 384 | Rh | Rh | 2 | 10 | 23 | 23 |
| 385 | Rh | Rh | 2 | 10 | 24 | 24 |
| 386 | Rh | Rh | 2 | 10 | 25 | 25 |
| 387 | Rh | Rh | 2 | 10 | 26 | 26 |
| 388 | Rh | Rh | 2 | 10 | 27 | 27 |
| 389 | Rh | Rh | 2 | 10 | 28 | 28 |
| 390 | Rh | Rh | 2 | 10 | 29 | 29 |
| 391 | Rh | Rh | 2 | 10 | 30 | 30 |
| 392 | Rh | Rh | 2 | 10 | 31 | 31 |
| 393 | Rh | Rh | 2 | 10 | 32 | 32 |
| 394 | Rh | Rh | 2 | 10 | 33 | 33 |
| 395 | Rh | Rh | 2 | 10 | 34 | 34 |
| 396 | Rh | Rh | 2 | 11 | 20 | 20 |
| 397 | Rh | Rh | 2 | 11 | 21 | 21 |
| 398 | Rh | Rh | 2 | 11 | 22 | 22 |
| 399 | Rh | Rh | 2 | 11 | 23 | 23 |
| 400 | Rh | Rh | 2 | 11 | 24 | 24 |

TABLE 9

| No  | M1 | M2 | n | P  | Q1 | Q2 |
|-----|----|----|---|----|----|----|
| 401 | Rh | Rh | 2 | 11 | 25 | 25 |
| 402 | Rh | Rh | 2 | 11 | 26 | 26 |
| 403 | Rh | Rh | 2 | 11 | 27 | 27 |
| 404 | Rh | Rh | 2 | 11 | 28 | 28 |
| 405 | Rh | Rh | 2 | 11 | 29 | 29 |

TABLE 9-continued

| No | M1 | M2 | n | P | Q1 | Q2 |
|---|---|---|---|---|---|---|
| 406 | Rh | Rh | 2 | 11 | 30 | 30 |
| 407 | Rh | Rh | 2 | 11 | 31 | 31 |
| 408 | Rh | Rh | 2 | 11 | 32 | 32 |
| 409 | Rh | Rh | 2 | 11 | 33 | 33 |
| 410 | Rh | Rh | 2 | 11 | 34 | 34 |
| 411 | Rh | Rh | 2 | 13 | 20 | 20 |
| 412 | Rh | Rh | 2 | 13 | 21 | 21 |
| 413 | Rh | Rh | 2 | 13 | 22 | 22 |
| 414 | Rh | Rh | 2 | 13 | 23 | 23 |
| 415 | Rh | Rh | 2 | 13 | 24 | 24 |
| 416 | Rh | Rh | 2 | 13 | 25 | 25 |
| 417 | Rh | Rh | 2 | 13 | 26 | 26 |
| 418 | Rh | Rh | 2 | 13 | 27 | 27 |
| 419 | Rh | Rh | 2 | 13 | 28 | 28 |
| 420 | Rh | Rh | 2 | 13 | 29 | 29 |
| 421 | Rh | Rh | 2 | 13 | 30 | 30 |
| 422 | Rh | Rh | 2 | 13 | 31 | 31 |
| 423 | Rh | Rh | 2 | 13 | 32 | 32 |
| 424 | Rh | Rh | 2 | 13 | 33 | 33 |
| 425 | Rh | Rh | 2 | 13 | 34 | 34 |
| 426 | Rh | Rh | 2 | 15 | 20 | 20 |
| 427 | Rh | Rh | 2 | 15 | 21 | 21 |
| 428 | Rh | Rh | 2 | 15 | 22 | 22 |
| 429 | Rh | Rh | 2 | 15 | 23 | 23 |
| 430 | Rh | Rh | 2 | 15 | 24 | 24 |
| 431 | Rh | Rh | 2 | 15 | 25 | 25 |
| 432 | Rh | Rh | 2 | 15 | 26 | 26 |
| 433 | Rh | Rh | 2 | 15 | 27 | 27 |
| 434 | Rh | Rh | 2 | 15 | 28 | 28 |
| 435 | Rh | Rh | 2 | 15 | 29 | 29 |
| 436 | Rh | Rh | 2 | 15 | 30 | 30 |
| 437 | Rh | Rh | 2 | 15 | 31 | 31 |
| 438 | Rh | Rh | 2 | 15 | 32 | 32 |
| 439 | Rh | Rh | 2 | 15 | 33 | 33 |
| 440 | Rh | Rh | 2 | 15 | 34 | 34 |
| 441 | Rh | Rh | 2 | 1 | 20 | 23 |
| 442 | Rh | Rh | 2 | 1 | 20 | 27 |
| 443 | Rh | Rh | 2 | 1 | 20 | 28 |
| 444 | Rh | Rh | 2 | 1 | 20 | 33 |
| 445 | Rh | Rh | 2 | 1 | 20 | 34 |
| 446 | Rh | Rh | 2 | 1 | 27 | 33 |
| 447 | Rh | Rh | 2 | 1 | 27 | 34 |
| 448 | Rh | Rh | 2 | 2 | 20 | 23 |
| 449 | Rh | Rh | 2 | 2 | 20 | 27 |
| 450 | Rh | Rh | 2 | 2 | 20 | 28 |

TABLE 10

| No | M1 | M2 | n | P | Q1 | Q2 |
|---|---|---|---|---|---|---|
| 451 | Rh | Rh | 2 | 2 | 20 | 33 |
| 452 | Rh | Rh | 2 | 2 | 20 | 34 |
| 453 | Rh | Rh | 2 | 2 | 27 | 33 |
| 454 | Rh | Rh | 2 | 2 | 27 | 34 |
| 455 | Rh | Rh | 2 | 4 | 20 | 23 |
| 456 | Rh | Rh | 2 | 4 | 20 | 27 |
| 457 | Rh | Rh | 2 | 4 | 20 | 28 |
| 458 | Rh | Rh | 2 | 4 | 20 | 33 |
| 459 | Rh | Rh | 2 | 4 | 20 | 34 |
| 460 | Rh | Rh | 2 | 4 | 27 | 33 |
| 461 | Rh | Rh | 2 | 4 | 27 | 34 |
| 462 | Rh | Rh | 2 | 10 | 20 | 23 |
| 463 | Rh | Rh | 2 | 10 | 20 | 27 |
| 464 | Rh | Rh | 2 | 10 | 20 | 28 |
| 465 | Rh | Rh | 2 | 10 | 20 | 33 |
| 466 | Rh | Rh | 2 | 10 | 20 | 34 |
| 467 | Rh | Rh | 2 | 10 | 27 | 33 |
| 468 | Rh | Rh | 2 | 10 | 27 | 34 |
| 469 | Rh | Rh | 2 | 15 | 20 | 23 |
| 470 | Rh | Rh | 2 | 15 | 20 | 27 |
| 471 | Rh | Rh | 2 | 15 | 20 | 28 |
| 472 | Rh | Rh | 2 | 15 | 20 | 33 |
| 473 | Rh | Rh | 2 | 15 | 20 | 34 |
| 474 | Rh | Rh | 2 | 15 | 27 | 33 |

TABLE 10-continued

| No | M1 | M2 | n | P | Q1 | Q2 |
|---|---|---|---|---|---|---|
| 475 | Rh | Rh | 2 | 15 | 27 | 34 |
| 476 | Pt | Pt | 1 | 1 | 20 | 20 |
| 477 | Pt | Pt | 1 | 1 | 23 | 23 |
| 478 | Pt | Pt | 1 | 1 | 26 | 26 |
| 479 | Pt | Pt | 1 | 1 | 27 | 27 |
| 480 | Pt | Pt | 1 | 1 | 28 | 28 |
| 481 | Pt | Pt | 1 | 1 | 33 | 33 |
| 482 | Pt | Pt | 1 | 1 | 34 | 34 |
| 483 | Pt | Pt | 1 | 2 | 20 | 20 |
| 484 | Pt | Pt | 1 | 2 | 23 | 23 |
| 485 | Pt | Pt | 1 | 2 | 26 | 26 |
| 486 | Pt | Pt | 1 | 2 | 27 | 27 |
| 487 | Pt | Pt | 1 | 2 | 28 | 28 |
| 488 | Pt | Pt | 1 | 2 | 33 | 33 |
| 489 | Pt | Pt | 1 | 2 | 34 | 34 |
| 490 | Pt | Pt | 1 | 4 | 20 | 20 |
| 491 | Pt | Pt | 1 | 4 | 23 | 23 |
| 492 | Pt | Pt | 1 | 4 | 26 | 26 |
| 493 | Pt | Pt | 1 | 4 | 27 | 27 |
| 494 | Pt | Pt | 1 | 4 | 28 | 28 |
| 495 | Pt | Pt | 1 | 4 | 33 | 33 |
| 496 | Pt | Pt | 1 | 4 | 34 | 34 |
| 497 | Pt | Pt | 1 | 7 | 20 | 20 |
| 498 | Pt | Pt | 1 | 7 | 23 | 23 |
| 499 | Pt | Pt | 1 | 7 | 26 | 26 |
| 500 | Pt | Pt | 1 | 7 | 27 | 27 |

TABLE 11

| No | M1 | M2 | n | P | Q1 | Q2 |
|---|---|---|---|---|---|---|
| 501 | Pt | Pt | 1 | 7 | 28 | 28 |
| 502 | Pt | Pt | 1 | 7 | 33 | 33 |
| 503 | Pt | Pt | 1 | 7 | 34 | 34 |
| 504 | Pt | Pt | 1 | 10 | 20 | 20 |
| 505 | Pt | Pt | 1 | 10 | 23 | 23 |
| 506 | Pt | Pt | 1 | 10 | 26 | 26 |
| 507 | Pt | Pt | 1 | 10 | 27 | 27 |
| 508 | Pt | Pt | 1 | 10 | 28 | 28 |
| 509 | Pt | Pt | 1 | 10 | 33 | 33 |
| 510 | Pt | Pt | 1 | 10 | 34 | 34 |
| 511 | Pt | Pt | 1 | 15 | 20 | 20 |
| 512 | Pt | Pt | 1 | 15 | 23 | 23 |
| 513 | Pt | Pt | 1 | 15 | 26 | 26 |
| 514 | Pt | Pt | 1 | 15 | 27 | 27 |
| 515 | Pt | Pt | 1 | 15 | 28 | 28 |
| 516 | Pt | Pt | 1 | 15 | 33 | 33 |
| 517 | Pt | Pt | 1 | 15 | 34 | 34 |
| 518 | Pt | Pt | 1 | 1 | 20 | 23 |
| 519 | Pt | Pt | 1 | 1 | 20 | 26 |
| 520 | Pt | Pt | 1 | 1 | 20 | 27 |
| 521 | Pt | Pt | 1 | 1 | 20 | 28 |
| 522 | Pt | Pt | 1 | 1 | 20 | 33 |
| 523 | Pt | Pt | 1 | 1 | 20 | 34 |
| 524 | Pt | Pt | 1 | 1 | 26 | 23 |
| 525 | Pt | Pt | 1 | 1 | 26 | 27 |
| 526 | Pt | Pt | 1 | 1 | 26 | 28 |
| 527 | Pt | Pt | 1 | 1 | 26 | 33 |
| 528 | Pt | Pt | 1 | 1 | 26 | 34 |
| 529 | Pt | Pt | 1 | 1 | 26 | 30 |
| 530 | Pt | Pt | 1 | 2 | 20 | 23 |
| 531 | Pt | Pt | 1 | 2 | 20 | 26 |
| 532 | Pt | Pt | 1 | 2 | 20 | 27 |
| 533 | Pt | Pt | 1 | 2 | 20 | 28 |
| 534 | Pt | Pt | 1 | 2 | 20 | 33 |
| 535 | Pt | Pt | 1 | 2 | 20 | 34 |
| 536 | Pt | Pt | 1 | 4 | 20 | 23 |
| 537 | Pt | Pt | 1 | 4 | 20 | 26 |
| 538 | Pt | Pt | 1 | 4 | 20 | 27 |
| 539 | Pt | Pt | 1 | 4 | 20 | 28 |
| 540 | Pt | Pt | 1 | 4 | 20 | 33 |
| 541 | Pt | Pt | 1 | 4 | 20 | 34 |
| 542 | Pt | Pt | 1 | 7 | 20 | 23 |
| 543 | Pt | Pt | 1 | 7 | 20 | 26 |

TABLE 11-continued

| No | M1 | M2 | n | P | Q1 | Q2 |
|---|---|---|---|---|---|---|
| 544 | Pt | Pt | 1 | 7 | 20 | 27 |
| 545 | Pt | Pt | 1 | 7 | 20 | 28 |
| 546 | Pt | Pt | 1 | 7 | 20 | 33 |
| 547 | Pt | Pt | 1 | 7 | 20 | 34 |
| 548 | Pt | Pt | 1 | 15 | 20 | 23 |
| 549 | Pt | Pt | 1 | 15 | 20 | 26 |
| 550 | Pt | Pt | 1 | 15 | 20 | 27 |

TABLE 12

| No | M1 | M2 | n | P | Q1 | Q2 |
|---|---|---|---|---|---|---|
| 551 | Pt | Pt | 1 | 15 | 20 | 28 |
| 552 | Pt | Pt | 1 | 15 | 20 | 33 |
| 553 | Pt | Pt | 1 | 15 | 20 | 34 |
| 554 | Pd | Pd | 1 | 1 | 20 | 20 |
| 555 | Pd | Pd | 1 | 1 | 23 | 23 |
| 556 | Pd | Pd | 1 | 1 | 26 | 26 |
| 557 | Pd | Pd | 1 | 1 | 27 | 27 |
| 558 | Pd | Pd | 1 | 1 | 28 | 28 |
| 559 | Pd | Pd | 1 | 1 | 33 | 33 |
| 560 | Pd | Pd | 1 | 1 | 34 | 34 |
| 561 | Pd | Pd | 1 | 2 | 20 | 20 |
| 562 | Pd | Pd | 1 | 2 | 23 | 23 |
| 563 | Pd | Pd | 1 | 2 | 26 | 26 |
| 564 | Pd | Pd | 1 | 2 | 27 | 27 |
| 565 | Pd | Pd | 1 | 2 | 28 | 28 |
| 566 | Pd | Pd | 1 | 2 | 33 | 33 |
| 567 | Pd | Pd | 1 | 2 | 34 | 34 |
| 568 | Pd | Pd | 1 | 4 | 20 | 20 |
| 569 | Pd | Pd | 1 | 4 | 23 | 23 |
| 570 | Pd | Pd | 1 | 4 | 26 | 26 |
| 571 | Pd | Pd | 1 | 4 | 27 | 27 |
| 572 | Pd | Pd | 1 | 4 | 28 | 28 |
| 573 | Pd | Pd | 1 | 4 | 33 | 33 |
| 574 | Pd | Pd | 1 | 4 | 34 | 34 |
| 575 | Pd | Pd | 1 | 7 | 20 | 20 |
| 576 | Pd | Pd | 1 | 7 | 23 | 23 |
| 577 | Pd | Pd | 1 | 7 | 26 | 26 |
| 578 | Pd | Pd | 1 | 7 | 27 | 27 |
| 579 | Pd | Pd | 1 | 7 | 28 | 28 |
| 580 | Pd | Pd | 1 | 7 | 33 | 33 |
| 581 | Pd | Pd | 1 | 7 | 34 | 34 |
| 582 | Pd | Pd | 1 | 10 | 20 | 20 |
| 583 | Pd | Pd | 1 | 10 | 23 | 23 |
| 584 | Pd | Pd | 1 | 10 | 26 | 26 |
| 585 | Pd | Pd | 1 | 10 | 27 | 27 |
| 586 | Pd | Pd | 1 | 10 | 28 | 28 |
| 587 | Pd | Pd | 1 | 10 | 33 | 33 |
| 588 | Pd | Pd | 1 | 10 | 34 | 34 |
| 589 | Pd | Pd | 1 | 15 | 20 | 20 |
| 590 | Pd | Pd | 1 | 15 | 23 | 23 |
| 591 | Pd | Pd | 1 | 15 | 26 | 26 |
| 592 | Pd | Pd | 1 | 15 | 27 | 27 |
| 593 | Pd | Pd | 1 | 15 | 28 | 28 |
| 594 | Pd | Pd | 1 | 15 | 33 | 33 |
| 595 | Pd | Pd | 1 | 15 | 34 | 34 |
| 596 | Pd | Pd | 1 | 1 | 20 | 23 |
| 597 | Pd | Pd | 1 | 1 | 20 | 26 |
| 598 | Pd | Pd | 1 | 1 | 20 | 27 |
| 599 | Pd | Pd | 1 | 1 | 20 | 28 |
| 600 | Pd | Pd | 1 | 1 | 20 | 33 |

TABLE 13

| No | M1 | M2 | n | P | Q1 | Q2 |
|---|---|---|---|---|---|---|
| 601 | Pd | Pd | 1 | 1 | 20 | 34 |
| 602 | Pd | Pd | 1 | 1 | 26 | 23 |
| 603 | Pd | Pd | 1 | 1 | 26 | 27 |
| 604 | Pd | Pd | 1 | 1 | 26 | 28 |
| 605 | Pd | Pd | 1 | 1 | 26 | 33 |

TABLE 13-continued

| No | M1 | M2 | n | P | Q1 | Q2 |
|---|---|---|---|---|---|---|
| 606 | Pd | Pd | 1 | 1 | 26 | 34 |
| 607 | Pd | Pd | 1 | 1 | 26 | 30 |
| 608 | Pd | Pd | 1 | 2 | 20 | 23 |
| 609 | Pd | Pd | 1 | 2 | 20 | 26 |
| 610 | Pd | Pd | 1 | 2 | 20 | 27 |
| 611 | Pd | Pd | 1 | 2 | 20 | 28 |
| 612 | Pd | Pd | 1 | 2 | 20 | 33 |
| 613 | Pd | Pd | 1 | 2 | 20 | 34 |
| 614 | Pd | Pd | 1 | 4 | 20 | 23 |
| 615 | Pd | Pd | 1 | 4 | 20 | 26 |
| 616 | Pd | Pd | 1 | 4 | 20 | 27 |
| 617 | Pd | Pd | 1 | 4 | 20 | 28 |
| 618 | Pd | Pd | 1 | 4 | 20 | 33 |
| 619 | Pd | Pd | 1 | 4 | 20 | 34 |
| 620 | Pd | Pd | 1 | 7 | 20 | 23 |
| 621 | Pd | Pd | 1 | 7 | 20 | 26 |
| 622 | Pd | Pd | 1 | 7 | 20 | 27 |
| 623 | Pd | Pd | 1 | 7 | 20 | 28 |
| 624 | Pd | Pd | 1 | 7 | 20 | 33 |
| 625 | Pd | Pd | 1 | 7 | 20 | 34 |
| 626 | Pd | Pd | 1 | 15 | 20 | 23 |
| 627 | Pd | Pd | 1 | 15 | 20 | 26 |
| 628 | Pd | Pd | 1 | 15 | 20 | 27 |
| 629 | Pd | Pd | 1 | 15 | 20 | 28 |
| 630 | Pd | Pd | 1 | 15 | 20 | 33 |
| 631 | Pd | Pd | 1 | 15 | 20 | 34 |
| 632 | Ru | Ru | 2 | 3 | 20 | 20 |
| 633 | Ru | Ru | 2 | 3 | 27 | 27 |
| 634 | Ru | Ru | 2 | 3 | 32 | 32 |
| 635 | Ru | Ru | 2 | 3 | 34 | 34 |
| 636 | Ru | Ru | 2 | 10 | 20 | 20 |
| 637 | Ru | Ru | 2 | 10 | 27 | 27 |
| 638 | Ru | Ru | 2 | 10 | 32 | 32 |
| 639 | Ru | Ru | 2 | 10 | 34 | 34 |
| 640 | Ru | Ru | 2 | 16 | 20 | 20 |
| 641 | Ru | Ru | 2 | 16 | 27 | 27 |
| 642 | Ru | Ru | 2 | 16 | 32 | 32 |
| 643 | Ru | Ru | 2 | 16 | 34 | 34 |
| 644 | Os | Os | 2 | 3 | 20 | 20 |
| 645 | Os | Os | 2 | 3 | 27 | 27 |
| 646 | Os | Os | 2 | 3 | 32 | 32 |
| 647 | Os | Os | 2 | 3 | 34 | 34 |
| 648 | Os | Os | 2 | 10 | 20 | 20 |
| 649 | Os | Os | 2 | 10 | 27 | 27 |
| 650 | Os | Os | 2 | 10 | 32 | 32 |

TABLE 14

| No | M1 | M2 | n | P | Q1 | Q2 |
|---|---|---|---|---|---|---|
| 651 | Os | Os | 2 | 10 | 34 | 34 |
| 652 | Os | Os | 2 | 16 | 20 | 20 |
| 653 | Os | Os | 2 | 16 | 27 | 27 |
| 654 | Os | Os | 2 | 16 | 32 | 32 |
| 655 | Os | Os | 2 | 16 | 34 | 34 |
| 656 | Ir | Rh | 2 | 1 | 20 | 20 |
| 657 | Ir | Rh | 2 | 1 | 23 | 23 |
| 658 | Ir | Rh | 2 | 1 | 26 | 26 |
| 659 | Ir | Rh | 2 | 1 | 27 | 27 |
| 660 | Ir | Rh | 2 | 1 | 28 | 28 |
| 661 | Ir | Rh | 2 | 1 | 33 | 33 |
| 662 | Ir | Rh | 2 | 1 | 34 | 34 |
| 663 | Ir | Rh | 2 | 2 | 20 | 20 |
| 664 | Ir | Rh | 2 | 2 | 23 | 23 |
| 665 | Ir | Rh | 2 | 2 | 26 | 26 |
| 666 | Ir | Rh | 2 | 2 | 27 | 27 |
| 667 | Ir | Rh | 2 | 2 | 28 | 28 |
| 668 | Ir | Rh | 2 | 2 | 33 | 33 |
| 669 | Ir | Rh | 2 | 2 | 34 | 34 |
| 670 | Ir | Rh | 2 | 4 | 20 | 20 |
| 671 | Ir | Rh | 2 | 4 | 23 | 23 |
| 672 | Ir | Rh | 2 | 4 | 26 | 26 |
| 673 | Ir | Rh | 2 | 4 | 27 | 27 |
| 674 | Ir | Rh | 2 | 4 | 28 | 28 |

TABLE 14-continued

| No | M1 | M2 | n | P | Q1 | Q2 |
|---|---|---|---|---|---|---|
| 675 | Ir | Rh | 2 | 4 | 33 | 33 |
| 676 | Ir | Rh | 2 | 4 | 34 | 34 |
| 677 | Ir | Rh | 2 | 10 | 20 | 20 |
| 678 | Ir | Rh | 2 | 10 | 23 | 23 |
| 679 | Ir | Rh | 2 | 10 | 26 | 26 |
| 680 | Ir | Rh | 2 | 10 | 27 | 27 |
| 681 | Ir | Rh | 2 | 10 | 28 | 28 |
| 682 | Ir | Rh | 2 | 10 | 33 | 33 |
| 683 | Ir | Rh | 2 | 10 | 34 | 34 |
| 684 | Ir | Rh | 2 | 15 | 20 | 20 |
| 685 | Ir | Rh | 2 | 15 | 23 | 23 |
| 686 | Ir | Rh | 2 | 15 | 26 | 26 |
| 687 | Ir | Rh | 2 | 15 | 27 | 27 |
| 688 | Ir | Rh | 2 | 15 | 28 | 28 |
| 689 | Ir | Rh | 2 | 15 | 33 | 33 |
| 690 | Ir | Rh | 2 | 15 | 34 | 34 |
| 691 | Pt | Pd | 1 | 1 | 20 | 20 |
| 692 | Pt | Pd | 1 | 1 | 23 | 23 |
| 693 | Pt | Pd | 1 | 1 | 26 | 26 |
| 694 | Pt | Pd | 1 | 1 | 27 | 27 |
| 695 | Pt | Pd | 1 | 1 | 28 | 28 |
| 696 | Pt | Pd | 1 | 1 | 33 | 33 |
| 697 | Pt | Pd | 1 | 1 | 34 | 34 |
| 698 | Pt | Pd | 1 | 2 | 20 | 20 |
| 699 | Pt | Pd | 1 | 2 | 23 | 23 |
| 700 | Pt | Pd | 1 | 2 | 26 | 26 |

TABLE 15

| No | M1 | M2 | n | P | Q1 | Q2 |
|---|---|---|---|---|---|---|
| 701 | Pt | Pd | 1 | 2 | 27 | 27 |
| 702 | Pt | Pd | 1 | 2 | 28 | 28 |
| 703 | Pt | Pd | 1 | 2 | 33 | 33 |
| 704 | Pt | Pd | 1 | 2 | 34 | 34 |
| 705 | Pt | Pd | 1 | 4 | 20 | 20 |
| 706 | Pt | Pd | 1 | 4 | 23 | 23 |
| 707 | Pt | Pd | 1 | 4 | 26 | 26 |
| 708 | Pt | Pd | 1 | 4 | 27 | 27 |
| 709 | Pt | Pd | 1 | 4 | 28 | 28 |
| 710 | Pt | Pd | 1 | 4 | 33 | 33 |
| 711 | Pt | Pd | 1 | 4 | 34 | 34 |
| 712 | Pt | Pd | 1 | 10 | 20 | 20 |
| 713 | Pt | Pd | 1 | 10 | 23 | 23 |
| 714 | Pt | Pd | 1 | 10 | 26 | 26 |
| 715 | Pt | Pd | 1 | 10 | 27 | 27 |
| 716 | Pt | Pd | 1 | 10 | 28 | 28 |
| 717 | Pt | Pd | 1 | 10 | 33 | 33 |
| 718 | Pt | Pd | 1 | 10 | 34 | 34 |
| 719 | Pt | Pd | 1 | 15 | 20 | 20 |
| 720 | Pt | Pd | 1 | 15 | 23 | 23 |
| 721 | Pt | Pd | 1 | 15 | 26 | 26 |
| 722 | Pt | Pd | 1 | 15 | 27 | 27 |
| 723 | Pt | Pd | 1 | 15 | 28 | 28 |
| 724 | Pt | Pd | 1 | 15 | 33 | 33 |
| 725 | Pt | Pd | 1 | 15 | 34 | 34 |
| 726 | Os | Ru | 1 | 1 | 20 | 20 |
| 727 | Os | Ru | 1 | 1 | 23 | 23 |
| 728 | Os | Ru | 1 | 1 | 26 | 26 |
| 729 | Os | Ru | 1 | 1 | 27 | 27 |
| 730 | Os | Ru | 1 | 1 | 28 | 28 |
| 731 | Os | Ru | 1 | 1 | 33 | 33 |
| 732 | Os | Ru | 1 | 1 | 34 | 34 |
| 733 | Os | Ru | 1 | 3 | 20 | 20 |
| 734 | Os | Ru | 1 | 3 | 23 | 23 |
| 735 | Os | Ru | 1 | 3 | 26 | 26 |
| 736 | Os | Ru | 1 | 3 | 27 | 27 |
| 737 | Os | Ru | 1 | 3 | 28 | 28 |
| 738 | Os | Ru | 1 | 3 | 33 | 33 |
| 739 | Os | Ru | 1 | 3 | 34 | 34 |
| 740 | Os | Ru | 1 | 4 | 20 | 20 |
| 741 | Os | Ru | 1 | 4 | 23 | 23 |
| 742 | Os | Ru | 1 | 4 | 26 | 26 |
| 743 | Os | Ru | 1 | 4 | 27 | 27 |

TABLE 15-continued

| No | M1 | M2 | n | P | Q1 | Q2 |
|---|---|---|---|---|---|---|
| 744 | Os | Ru | 1 | 4 | 28 | 28 |
| 745 | Os | Ru | 1 | 4 | 33 | 33 |
| 746 | Os | Ru | 1 | 4 | 34 | 34 |
| 747 | Os | Ru | 1 | 10 | 20 | 20 |
| 748 | Os | Ru | 1 | 10 | 23 | 23 |
| 749 | Os | Ru | 1 | 10 | 26 | 26 |
| 750 | Os | Ru | 1 | 10 | 27 | 27 |

TABLE 16

| No | M1 | M2 | n | P | Q1 | Q2 |
|---|---|---|---|---|---|---|
| 751 | Os | Ru | 1 | 10 | 28 | 28 |
| 752 | Os | Ru | 1 | 10 | 33 | 33 |
| 753 | Os | Ru | 1 | 10 | 34 | 34 |
| 754 | Os | Ru | 1 | 15 | 20 | 20 |
| 755 | Os | Ru | 1 | 15 | 23 | 23 |
| 756 | Os | Ru | 1 | 15 | 26 | 26 |
| 757 | Os | Ru | 1 | 15 | 27 | 27 |
| 758 | Os | Ru | 1 | 15 | 28 | 28 |
| 759 | Os | Ru | 1 | 15 | 33 | 33 |
| 760 | Os | Ru | 1 | 15 | 34 | 34 |

The metal coordination compound of the formula (1) according to the present invention may be synthesized through the following reaction schemes representing a synthesis process of iridium complex as an example.

$$IrCl_3 + 4L \rightarrow L_2IrCl_2IrL_2 \quad (1)$$

$$L_2IrCl_2IrL_2 + 2Hacac \rightarrow 2IrL_2(acac) \quad (2)$$

$$2IrL_2(acac) + L' \rightarrow L_2IrL'L_2 \quad (3)$$

Hacac: acetylacetone acac: dehydrogenated acetylacetone

First, according to the scheme (1), a binuclear iridium complex bridged with chlorine is synthesized and then made into its acetylacetone derivative (the scheme (2)), followed by reaction with L' to obtain an objective binuclear iridium complex (the scheme (3)).

Hereinafter, the present invention will be described more specifically used on Examples.

EXAMPLE 1

Figure 1C:
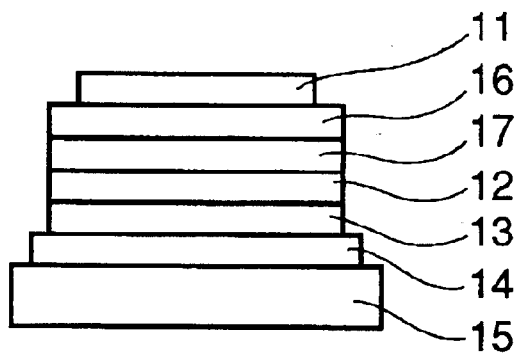

An organic luminescence device (EL device) having a structure shown in FIG. 1C was prepared in the following manner.

On a glass substrate (transparent substrate 15), a 100 nm-thick film (transparent electrode 14) of ITO (indium tin oxide) was formed by sputtering, followed by patterning.

On the ITO-formed substrate, four organic layers and two metal electrode layers shown below were successively formed by vacuum (vapor) deposition using resistance heating in a vacuum chamber ($10^{-4}$ Pa).

Organic layer 1 (hole transport layer 13) (50 nm): α-NPD

Organic layer 2 (luminescence layer 12) (40 nm): co-deposited film of CBP: metal coordination compound of formula 1 shown below (93:7 by weight)

Organic layer 3 (exciton diffusion prevention layer 17) (20 nm): BCP

Organic layer 4 (electron transport layer 16) (40 nm): Alq3

Metal electrode layer 1 (metal electrode 11) (15 nm): Al—Li alloy (Li=1.8 wt. %)

Metal electrode layer 2 (metal electrode 11) (100 nm): Al

The metal electrode layers 1 and 2 were patterned to have an effective luminescence area (opposing electrode area) of 3 mm².

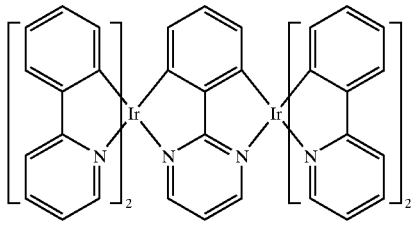

EL characteristics of the thus-prepared organic luminescence device using the metal coordination compounds of formula (1) (Ex. Comp. No. (1)) was measured by using a microammeter ("Model 4140B", mfd. by Hewlett-Packard Co.) for a current-voltage characteristic) and a spectrophotofluoro-meter ("Model SR1", mfd. by Topcon K. K.) for emission. The organic luminescence device exhibited good rectification characteristic.

When a voltage of 12 volts was applied to the organic luminescence device, good luminescence from the device was confirmed. This luminescence was similar to photoluminescence obtained when a toluene solution of the luminescence material (the metal coordination compound (Ex. Comp. No. 1), was used. Accordingly, it was confirmed that the luminescence from the organic luminescence device was that resulting from the luminescence material.

When the organic luminescence device was continuously driven for 150 hours, the organic luminescence device produced stable luminescence.

EXAMPLE 2

An organic luminescence device was prepared and evaluated in the same manner as in Example 1 except for using the following metal coordination compound (Ex. Comp. No. 46) shown below in place of the metal coordination compound (Ex. Comp. No. 1).

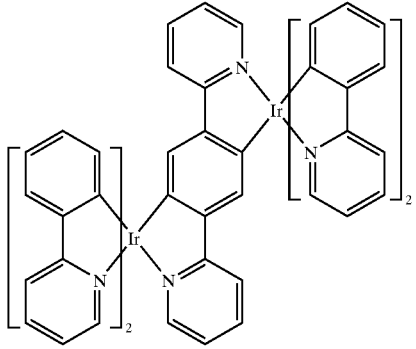

As a result when a voltage of 12 volts was applied to the organic luminescence device, good luminescence resulting from the luminescence material (the metal coordination compound (Ex. Comp. No. 46) was confirmed.

When the organic luminescence device was continuously driven for 150 hours, the organic luminescence device produced stable luminescence.

EXAMPLE 3

Figure 2:
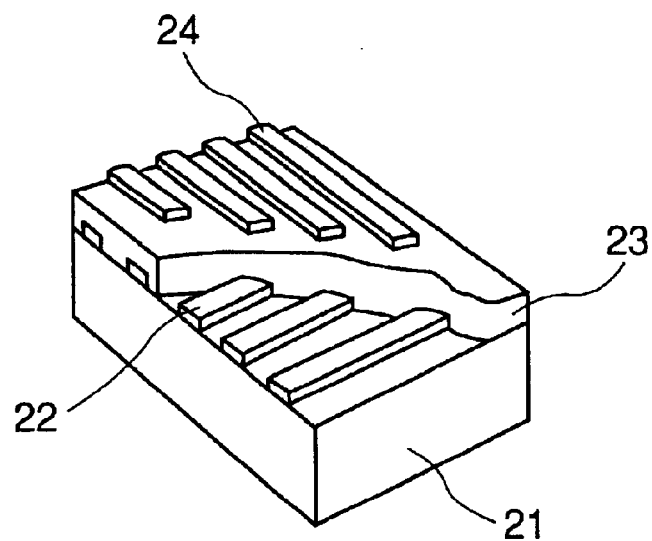
FIG. 2 illustrates a simple matrix-type organic EL device according to Example 3.

A simple matrix-type organic luminescence device having a structure shown in FIG. 2 was prepared in the following manner.

On a glass substrate 21 measuring 75 mm-length, 75 mm-width and 1.1 mm-thickness, a ca. 100 nm-thick ITO film was formed by sputtering and patterned into 100 lines of 100 μm-wide transparent matrix electrodes (anode side) with a spacing of 40 μm as simple matrix electrodes. Then, a four-layered organic compound layer 23 was formed thereon including a luminescence layer 12 containing the metal coordination compound (Ex. Comp. No. 1) in the same manner as in Example 1.

Then, 100 lines of 100 μm-wide metal electrodes 24 were formed with a spacing of 40 μm by mask vacuum deposition so as to be perpendicular to the transparent electrodes by vacuum deposition at a vacuum of $2.7 \times 10^{-3}$ Pa ($2 \times 10^{-5}$ Torr). The metal electrodes were formed as a lamination of 10 nm-thick layer of Al/Li alloy (Li: 1.3 wt. %) and then 150 nm-thick layer of Al.

Figure 3:
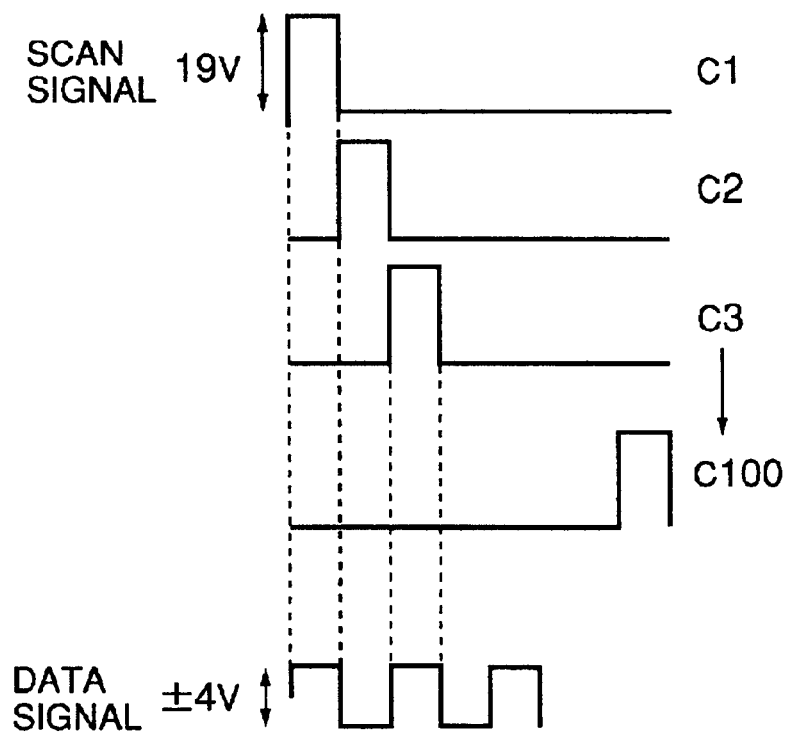
FIG. 3 illustrates drive signals used in Example 3.

The thus-obtained 100×100-simple matrix-type organic luminescence device was subjected to a simple matrix drive in a glove box filled with nitrogen at voltages of 15 volts to 23 volts by using a scanning signal of 19 volts and data signals of ±4 volts as shown in FIG. 3. As a result of an interlaced drive at a frame frequency of 30 Hz, smooth motion pictures were confirmed.

EXAMPLE 4

Synthesis of Ex. Comp. No. 46

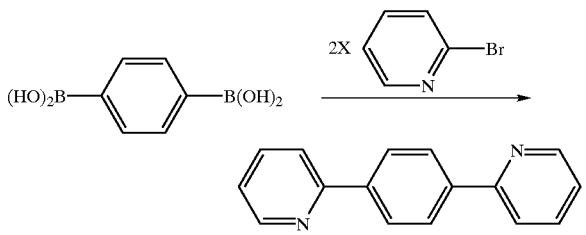

In a 1 L (litter)-three-necked flask, 10.00 g (60.3 mmol) of 1,4-phenylenebisboronic acid, 19.1 g (121 mmol) of 1-bromopyridine, 120 ml of toluene, 60 ml of ethanol and 25 ml of 2M-sodium carbonate aqueous solution, were placed and stirred at room temperature under a nitrogen stream, followed by addition of 4.74 g (4.10 mmol) of tetrakis(triphenylphosphine)palladium (0). Thereafter, the system was refluxed under stirring and nitrogen stream for 8 hours. After completion of the reaction, the reaction product was cooled and extracted by adding cold water and toluene. The organic layer was washed with saline water and dried with anhydrous magnesium sulfate, followed by removal of the solvent under a reduced pressure to provide dry solid. The residue was purified by silica gel column chromatography (eluent: toluene/ethyl acetate=2/1) to obtain 7.8 g (yield=56%) of 1,4-bis(2-pyridyl)benzene.

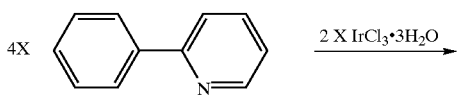

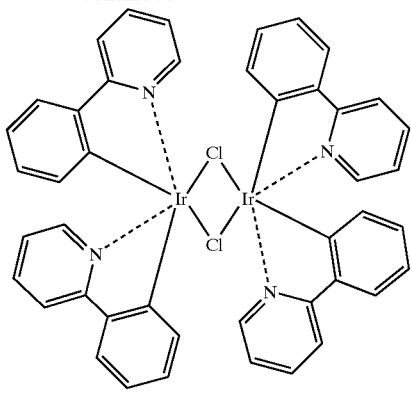

In a 10 L-three-necked flask, 50.0 g (142 mmol) of iridium (III) chloride trihydrate (mfd. by Across Co.), 98 g (631 mmol) of 2-phenylpyridine (mfd. by Aldrich Co.), 3870 ml of ethoxyethanol and 1290 ml of distilled water were placed and stirred for 30 min. at room temperature under nitrogen stream, followed by 24 hours of reflux under stirring. The reaction product was cooled to room temperature, and the precipitate was recovered by filtration and washed successively with water, ethanol and acetone. After being dried at room temperature under a reduced pressure, the dried product was dissolved in 9700 ml of methylene chloride to remove an insoluble matter by filtration. To the filtrate, 3200 ml of toluene and 1300 ml of hexane were added, followed by distilling-off of the solvent under reduced pressure until the volume thereof was reduced to 6400 ml. The resultant liquid was cooled on an ice bath to precipitate a crystal. The crystal was recovered by filtration to obtain 49.5 g (Yield: 65.1%) of tetrakis (2-phenylpyridine-$C^2$,N)($\mu$-dichloro)diiridium (III).

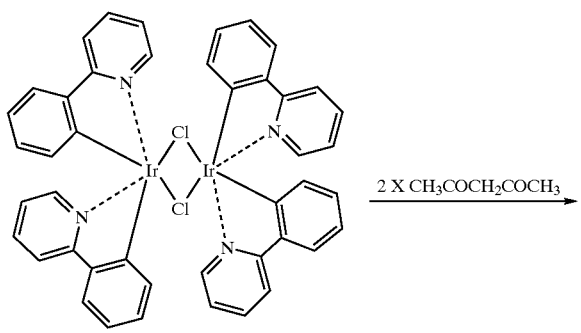

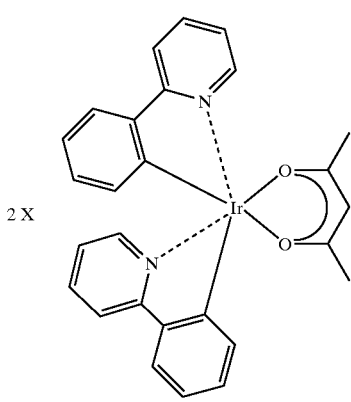

In a 3 L-three-necked flask, 1250 ml of ethoxyethanol, 41.8 g (39.0 mmol) of tetrakis(2-phenylpyridine-$C^2$,N)($\mu$-dichloro)diiridium, 10.0 g (99.9 mmol) of acetylacetone and 45.0 g (425 mmol) of sodium carbonate, were placed and stirred for 1 hour at room temperature under an argon stream, followed by 15 hours of reflux under stirring. The reaction product was cooled with ice, and the precipitate was filtered out and washed with water. The precipitate was successively washed with diethyl ether and hexane and was purified by silica gel chromatography (eluent: methylene chloride) followed by washing with hexane) to obtain 26.0 g (yield: 55.3%) of bis(2-phenyl-pyridine-$C^2$,N) (acetylacetonato)iridium (III).

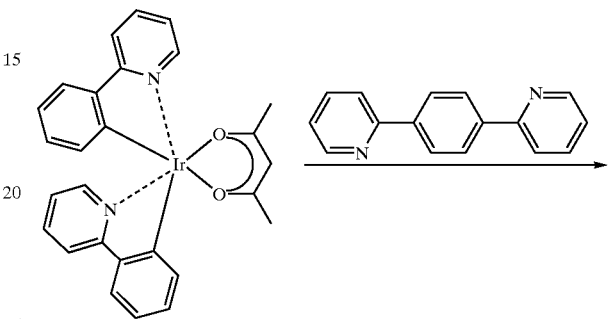

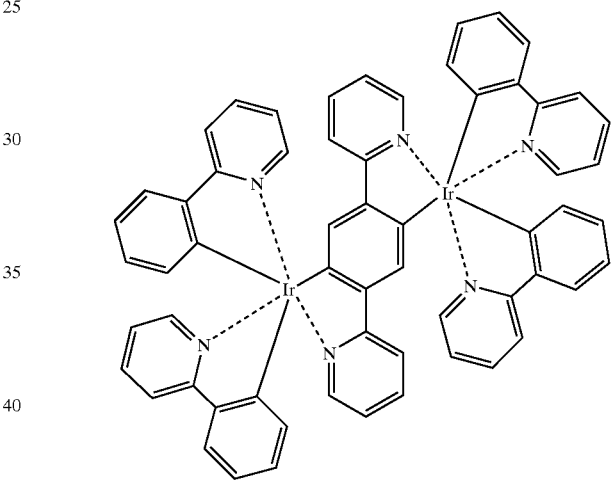

In a 3 L-three-necked flask, 1520 ml of glycerol was placed and subjected to bubbling with argon stream for 30 minutes on an oil bath held around 170° C. Under the argon stream, to the glycerol, 1.81 g (7.79 mmol) of 1,4-bis(2-pyridyl)benzene was added and dissolved therein, followed by addition of 19.00 g (31.52 mmol) of bis(2-phenylpyridine-$C^2$ N)(acetyl-acetonato)iridium (III). The system was gradually heated and stirred for 3 hours around 180° C. (inner temperature). After the reaction, the reaction mixture was cooled to room temperature and poured into 15 liters of ice water to precipitate a crystal. The crystal was filtered out and washed with water, followed by washing with 1.5 liters of diethyl ether under stirring. The crystal was purified by silica gel column chromatography (eluent: toluene/methylene chloride=1/1) to obtain 2.81 g (Yield: 29.3%) of a red powdery objective compound (Ex. Comp. No. 46).

The compound was subjected to MALDI-TOF MS (matrix-assisted laser desorption ionization time-of-flight mass spectroscopy), whereby M⁺ (a mass of an ion obtained by removing one electron from the compound) thereof of 1232.3 was confirmed.

EXAMPLE 5

The metal coordination compound (Ex. Comp. No. 46) prepared in Example 4 was subjected to emission spectrum analysis in a toluene solution and a powdery (solid) state.

Figure 4:
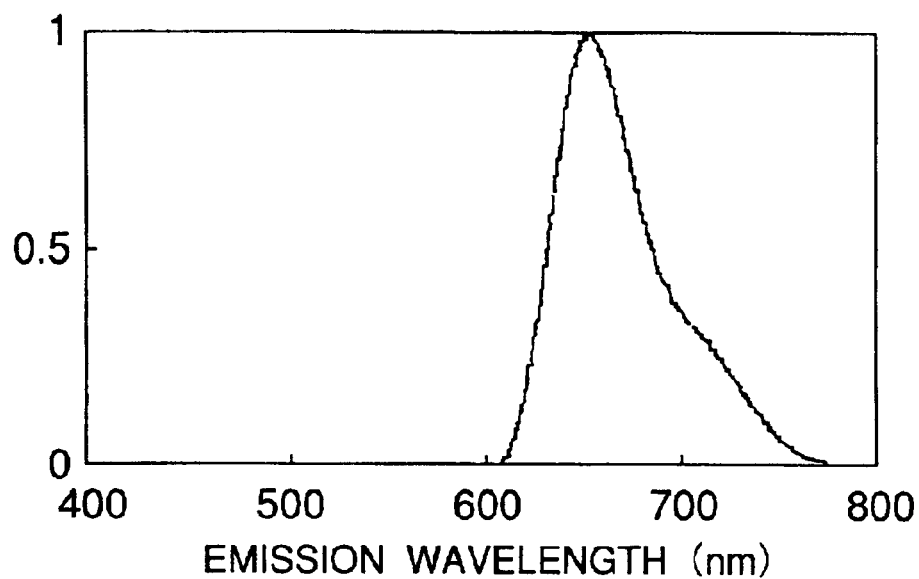
FIG. 4 is an emission spectrum diagram of a metal coordination compound of the present invention in a solution state used in Example 5.
Figure 5:
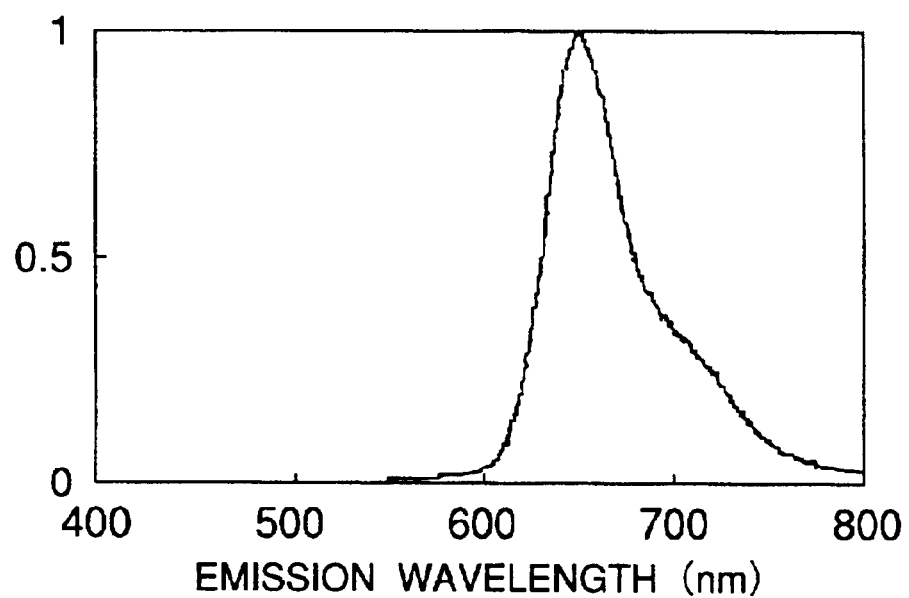
FIG. 5 is an emission spectrum diagram of a metal coordination compound of the present invention in a powdery state used in Example 5.

FIG. 4 was an emission spectrum chart (exciting light: 550 nm) of the compound in the toluene solution at a concentration of $5 \times 10^{-6}$ mol/l, and FIG. 5 was an emission spectrum chart (exciting light: 550 nm) of the compound in the powdery state.

The measured peak emission spectrum wavelength of the compound in the toluene solution was 651 nm and that of the compound in the powdery state was 655 nm.

As a result, it has been confirmed that the metal coordination compound of the formula (1) according to the present invention produced strong luminescence even in a powdery state wherein ordinary luminescent materials were liable to cause concentration extinction and provided the emission spectrum (in the powdery state) substantially equal to that in the low-concentration toluene solution, thus possessing a good concentration extinction-suppression performance.

Generally, an emission spectrum of a metal coordination compound in a powdery (solid) state is liable to be shifted to the longer wavelength side and have a broaden spectrum shape. In this state, a resultant luminescence intensity is generally lowered.

On the other hand, the metal coordination compound of the present invention produced strong luminescence. This may be attributable to a particular molecular structure of the metal coordination compound of the present invention such that the center metals are surrounded by the ligands to be less liable to be affected by a surrounding substance.

Incidentally, when the metal coordination compound (Ex. Comp. No. 46) used in this example was compared with $Ir(ppy)_3$, the metal coordination compound is characterized by its center quadridentate ligand having three rings.

$Ir(ppy)_3$ shows an emission spectrum having a peak wavelength of 515 nm. On the other hand, the metal coordination compound shows the peak emission spectrum wavelength of 655 nm as described above, thus being largely shifted to the longer wavelength side. This may be attributable to the center quadridentate ligand having three rings of the metal coordination compound (Ex. Comp. No. 46) contributing to luminescence, not the phenylpyridine ligand as in $Ir(ppy)_3$.

Accordingly, luminescence from the metal coordination compound (Ex. Comp. No. 46) as the luminescence material used in the present invention may be considered to be one from the MLCT excited state based on the center quadridentate ligand having three rings.

EXAMPLE 6

Figure 1D:
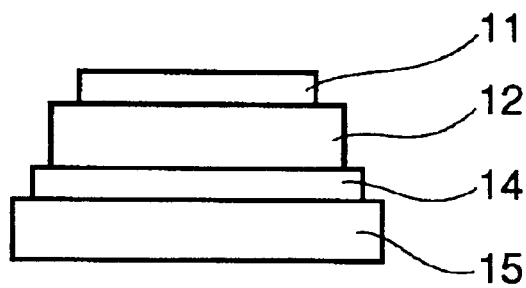

An organic luminescence device having a single organic layer as a luminescence layer 12 as shown in FIG. 1D was prepared in the following manner.

On a glass substrate 15, a 100 nm-thick ITO film 14 was formed by sputtering and patterned.

Onto the ITO film, a solution for the luminescence layer 12 of 10 mg of the metal coordination compound (Ex. Comp. No. 46) and 90 mg of polyvinyl carbazole (average molecular weight of 9600) in 10 g of chlorobenzene was applied by spin coating (2000 rpm, 20 sec) in a nitrogen atmosphere, followed by hot curing for 1 hour at 80° C. to obtain a 120 nm-thick luminescence layer 12 (single organic layer).

After the thus-treated substrate was set in a vacuum deposition chamber, a cathode 11 having the following two-layer electrode structure was formed by sputtering, followed by patterning to have an effective luminescence area (opposing electrode area) of 3 $mm^2$.

Metal electrode layer 1 (cathode 11) (15 nm): Al—Li alloy (Li=1.8 wt. %)

Metal electrode layer 2 (cathode 11) (100 nm): Al

The thus-prepared organic luminescence device was supplied with a DC voltage between the ITO side (14) as the anode and the Al side (11) as the cathode.

As a result, the device showed a good rectification (current) characteristic of 12 $mA/cm^2$ under application of 15 volts.

When the device was subjected to measurement of an emission spectrum by using a spectrophoto-fluorometer ("Model SR1", mfd. by Topcon K. K.), the resultant emission spectrum showed a peak wavelength of 655 nm and a shape substantially identical to those in the powdery state in Example 5.

Light emission from the device was clear red luminescence by eye observation and stable even when the device was continuously driven for 200 hours.

EXAMPLE 7

An organic luminescence device was prepared and evaluated in the same as in Example 6 except that a solution for the luminescence layer 12 was prepared by using 30 mg of the metal coordination compound (Ex. Comp. No. 46), 70 mg of polyvinyl carbazole (average molecular weight of 9600) and 10 g of chlorobenzene.

The resultant performances and the resultant emission spectrum of the device were similar to those obtained in Example 6.

EXAMPLE 8

An organic luminescence device was prepared and evaluated in the same manner as in Example 6 except that a 90 nm-thick luminescence layer 12 was formed with a solution of 10 mg of the metal coordination compound (Ex. Comp. No. 46) in 1 g of chlorobenzene by spin coating (1500 rpm, 10 sec) in a nitrogen atmosphere.

As a result, the device showed a good rectification (current) characteristic of 8 $mA/cm^2$ under application of 16 volts.

Further, the device showed a peak emission spectrum wavelength of 660 nm and a shape substantially identical to those in the powdery state in Example 5.

Light emission from the device was clear red luminescence by eye observation and stable even when the device was continuously driven for 100 hours.

As described above, according to the present invention, the metal coordination compound of the formula (1), which was a binuclear molecular structure characterized by a center quadridentate ligand and surrounding bidentate ligands, exhibits a high phosphorescence yield and has a shorter phosphorescence life. Thus, this compound is suitable as a luminescence material for an organic EL device. Furthermore, the resultant organic EL device (organic luminescence device) having an organic layer comprising the metal coordination compound of the formula (1) exhibits excellent performance including not only a high-efficiency luminescence, but also a high luminance for a long period and less deterioration by continuous energizing. The organic EL device is also excellent as a display device.

What is claimed is:

1. A metal coordination compound represented by the following formula (1):

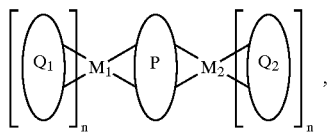   (1)

wherein M1 and M2 independently denote a metal atom selected from the group consisting of Ir, Pt, Rh, Pd, Ru and Os; P is a quadridentate ligand connected to M1 and M2; Q1 is a bidentate ligand connected to M1; Q2 is a bidentate ligand connected to M2; and n is 1 or 2, wherein the bidentate ligand Q1 is represented by formula (2) shown below and the bidentate lingand Q2 is represented by formula (3) shown below:

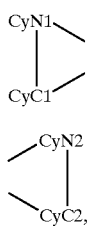

wherein CyN1 and CyN2 are each a cyclic group capable of having a substituent, including a nitrogen atom and bonded to the metal atom M1 or M2 via the nitrogen atom: CyC1 and CyC2 are each a cyclic group capable of having a substituent, including a carbon atom and bonded to the metal atom M1 or M2 via the carbon atom, with a proviso that the cyclic group CyN1 and the cyclic group CyC1 are bonded to each other via a covalent bond and the cyclic group CyN2 and the cyclic group CyC2 are bonded to each other via a covalent bond, and wherein the optional substituent of the cyclic groups is selected from the group consisting of:
a halogen atom;
a cyano group;
a nitro group;
a trialkylsilyl group of which the alkyl groups are independently a linear or branched alkyl group having 1 to 8 carbon atoms; a linear or branched alkyl group having 1 to 20 carbon atoms of which the alkyl group can include one or non-neighboring two or more methylene groups that can be replaced with —O—, —S—, —C(O)—, —C(O)—O—, —O—C(O)—, —CH=CH— or —C≡C—, and the alkyl group can include a hydrogen atom that can be optionally replaced with a fluorine atom; and an aromatic group capable of having a substituent, which is a halogen atom, a cyano atom, a nitro atom, a linear or branched alkyl group having 1 to 20 carbon atoms of which the alkyl group can include one or non-neighboring two or more methylene groups that can be replaced with —O—, —S—, —C(O)—, —C(O)—O—, —O—C(O)—, —CH=CH— or —C≡C—, and the alkyl group can include a hydrogen atom that can be optionally replaced with a fluorine atom.

2. A compound according to claim 1, wherein the quadridentate ligand P is connected to the metal atoms M1 and M2 each via a carbon atom, an oxygen atom or a nitrogen atom.

3. A compound according to claim 1, wherein the metal atom M1 is identical in species to the metal atom M2.

4. A compound according to claim 1, wherein the bidentate ligand Q1 is identical to the bidentate ligand Q2.

5. A compound according to claim 1, wherein the bidentate ligands Q1 and Q2 are each a carrier-transporting ligand, and the quadridentate ligand P is a luminescent ligand.

6. An organic luminescence device, comprising: a pair of electrodes disposed on a substrate, and a luminescence layer comprising at least one organic compound disposed between the electrodes, said organic compound comprising at least one species of a metal coordination compound of the formula (1) according to claim 1.

7. A device according to claim 6, wherein a voltage is applied between the electrodes to produce phosphorescence.

8. A device according to claim 6, wherein the luminescence layer further comprises a carrier-transporting compound.

9. A device according to claim 6, wherein the luminescence layer is consisting only of the metal coordination compound.

* * * * *

UNITED STATES PATENT AND TRADEMARK OFFICE
CERTIFICATE OF CORRECTION

PATENT NO. : 6,783,873 B2
DATED : August 31, 2004
INVENTOR(S) : Akira Tsuboyama et al.

Page 1 of 1

It is certified that error appears in the above-identified patent and that said Letters Patent is hereby corrected as shown below:

Title page,
Item [57], ABSTRACT,
Line 5, "M1;" should read -- M2; --.

Column 4,
Line 3, "a-singlet" should read -- a singlet --; and
Line 38, "M1;" should read -- M2; --.

Column 32,
Line 56, "was" should read -- has --.

Signed and Sealed this

Fifth Day of April, 2005

JON W. DUDAS
*Director of the United States Patent and Trademark Office*